US009901600B2

(12) United States Patent
Mitsialis et al.

(10) Patent No.: US 9,901,600 B2
(45) Date of Patent: Feb. 27, 2018

(54) METHODS AND COMPOSITIONS RELATING TO MESENCHYMAL STEM CELL EXOSOMES

(75) Inventors: S. Alexander Mitsialis, Newton, MA (US); Changjin Lee, Boston, MA (US); Stella Kourembanas, Newton, MA (US)

(73) Assignee: Children's Medical Center Corporation, Boston, MA (US)

( * ) Notice: Subject to any disclaimer, the term of this patent is extended or adjusted under 35 U.S.C. 154(b) by 701 days.

(21) Appl. No.: 14/004,237

(22) PCT Filed: Mar. 9, 2012

(86) PCT No.: PCT/US2012/028524
§ 371 (c)(1),
(2), (4) Date: Nov. 20, 2013

(87) PCT Pub. No.: WO2012/125471
PCT Pub. Date: Sep. 20, 2012

(65) Prior Publication Data
US 2014/0065240 A1    Mar. 6, 2014

Related U.S. Application Data

(60) Provisional application No. 61/451,981, filed on Mar. 11, 2011.

(51) Int. Cl.
*A61K 35/407* (2015.01)
*A61K 31/00* (2006.01)
*C12N 5/00* (2006.01)
*C12N 5/02* (2006.01)
*A61K 35/28* (2015.01)
*A61K 35/42* (2015.01)
*A61K 38/17* (2006.01)
*A61K 45/06* (2006.01)
*A61K 9/00* (2006.01)
*A61K 47/10* (2017.01)
*C12N 5/0775* (2010.01)

(52) U.S. Cl.
CPC ............ *A61K 35/28* (2013.01); *A61K 9/0019* (2013.01); *A61K 9/0078* (2013.01); *A61K 35/42* (2013.01); *A61K 38/1709* (2013.01); *A61K 45/06* (2013.01); *A61K 47/10* (2013.01); *C12N 5/0663* (2013.01)

(58) Field of Classification Search
None
See application file for complete search history.

(56) References Cited

U.S. PATENT DOCUMENTS

| 6,685,911 B1 * | 2/2004 | Zitvogel | A61K 38/1709 424/1.21 |
| 8,476,017 B2 | 7/2013 | Pietrzkowski | |
| 2004/0214783 A1 * | 10/2004 | Terman | A61K 39/0011 514/33 |
| 2006/0286089 A1 | 12/2006 | Berenson et al. | |
| 2011/0003008 A1 | 1/2011 | Lim | |
| 2013/0143314 A1 | 6/2013 | Shiels et al. | |

FOREIGN PATENT DOCUMENTS

| CN | 101890050 A | 11/2010 |
| JP | 2008-525490 A | 7/2008 |
| KR | 20120002361 A | 1/2012 |
| WO | WO 2006/071796 A2 | 7/2006 |
| WO | WO 2007/027156 A1 | 3/2007 |
| WO | WO 2008/020815 A1 | 2/2008 |
| WO | WO 2008/060788 A2 | 5/2008 |
| WO | WO 2009/105044 A1 | 8/2009 |
| WO | WO 2011/010966 A1 | 1/2011 |
| WO | WO 2011/053257 A2 | 5/2011 |
| WO | WO 2012/115885 A1 | 8/2012 |
| WO | WO 2013/150303 A1 | 10/2013 |
| WO | WO 2015/179227 A1 | 11/2015 |

OTHER PUBLICATIONS

PCT/US2012/028524, dated Sep. 26, 2013, International Preliminary Report on Patentability.
PCT/US2012/028524, dated Jun. 8, 2012, International Search Report and Written Opinion.
Bruno et al., Mesenchymal stem cell-derived microvesicles protect against acute tubular injury. J Am Soc Nephrol. May 2009;20(5):1053-67. doi: 10.1681/ASN.2008070798. Epub Apr. 23, 2009.
Gupta et al., Intrapulmonary delivery of bone marrow-derived mesenchymal stem cells improves survival and attenuates endotoxin-induced acute lung injury in mice. J Immunol. Aug. 1, 2007;179(3):1855-63.
Lai et al., Exosome secreted by MSC reduces myocardial ischemia/reperfusion injury. Stem Cell Res. May 2010;4(3):214-22. doi: 10.1016/j.scr.2009.12.003. Epub Jan. 4, 2010.
Lee et al., Exosomes Mediate the Cytoprotective Effects of Bone Marrow-Derived Stromal Cells (MSCs) on the Hypoxic Lung. American Thoracic Society International Conference Abstracts. May 13-18, 2011. Abstract 21620.
Lee et al., Intravenous hMSCs improve myocardial infarction in mice because cells embolized in lung are activated to secrete the anti-inflammatory protein TSG-6. Cell Stem Cell. Jul. 2, 2009;5(1):54-63. doi: 10.1016/j.stem.2009.05.003.
Mei et al., Prevention of LPS-induced acute lung injury in mice by mesenchymal stem cells overexpressing angiopoietin 1. PLoS Med. Sep. 2007;4(9):e269, pp. 1525-1537.

(Continued)

*Primary Examiner* — Chris R Tate
*Assistant Examiner* — Douglas F White
(74) *Attorney, Agent, or Firm* — Wolf, Greenfield & Sacks, P.C.

(57) ABSTRACT

The invention provides compositions comprising mesenchymal stem cell (MSC) derived exosomes, and methods of their use in subjects having certain lung diseases including inflammatory lung disease.

15 Claims, 29 Drawing Sheets

(56) References Cited

OTHER PUBLICATIONS

Ortiz et al., Mesenchymal stem cell engraftment in lung is enhanced in response to bleomycin exposure and ameliorates its fibrotic effects. Proc Natl Acad Sci U S A. Jul. 8, 2003;100(14):8407-11. Epub Jun. 18, 2003.
Rojas et al., Bone marrow-derived mesenchymal stem cells in repair of the injured lung. Am J Respir Cell Mol Biol. Aug. 2005;33(2):145-52. Epub May 12, 2005.
Spees et al., Bone marrow progenitor cells contribute to repair and remodeling of the lung and heart in a rat model of progressive pulmonary hypertension. FASEB J. Apr. 2008;22(4):1226-36.
Xu et al., Prevention of endotoxin-induced systemic response by bone marrow-derived mesenchymal stem cells in mice. Am J Physiol Lung Cell Mol Physiol. Jul. 2007;293(1):L131-41. Epub Apr. 6, 2007.
Aslam et al., Bone marrow stromal cells attenuate lung injury in a murine model of neonatal chronic lung disease. Am J Respir Crit Care Med. Dec. 1, 2009;180(11):1122-30. Epub Aug. 27, 2009.
Bonfield et al., Adult mesenchymal stem cells: an innovative therapeutic for lung diseases. Discov Med. Apr. 2010;9(47):337-45. Retrieved from the interne May 25, 2012 viahttp://www.discoverymedicine/com/Tracey-L-Bonfield/2010/04/15/adult-mesenchymal-stem-cells-an-innovative-therapeutic-for-lung-diseases/.
Gotts et al., Mesenchymal stem cells and acute lung injury. Crit Care Clin. Jul. 2011;27(3):719-33. Epub May 23, 2011.
Katsha et al., Paracrine factors of multipotent stromal cells ameliorate lung injury in an elastase-induced emphysema model. Mol Ther. Jan. 2011;19(1):196-203. Epub Sep. 14, 2010.
Matthay et al., Mesenchymal stem cells for acute lung injury: preclinical evidence. Crit Care Med. Oct. 2010;38(10 Suppl):S569-73.
Musina et al., Comparison of mesenchymal stem cells obtained from different human tissues. Bull Exp Biol Med. Apr. 2005;139(4):504-9.
Patel et al., Mesenchymal stem cells attenuate hypoxic pulmonary vasoconstriction by a paracrine mechanism. J Surg Res. Dec. 2007;143(2):281-5. Epub Sep. 14, 2007.
Van Haaften et al., Airway delivery of mesenchymal stem cells prevents arrested alveolar growth in neonatal lung injury in rats. Am J Respir Crit Care Med. Dec. 1, 2009;180(11):1131-42. Epub Aug. 27, 2009.
Weiss et al., Embryonic stem cells and repair of lung injury. Mol Ther. Mar. 2010;18(3):460-1.
PCT/US2015/031008, dated Aug. 28, 2015, International Search Report and Written Opinion.
Choi et al., Proteomic analysis of microvesicles derived from human colorectal cancer ascites. Proteomics. Jul. 2011;ll(13):2745-51. doi: 10.1002/pmic.201100022. Epub Jun. 1, 2011.
Gallo et al., The majority of microRNAs detectable in serum and saliva is concentrated in exosomes. PLoS One. 2012;7(3):e30679. doi: 10.1371/journal.pone.0030679. Epub Mar. 9, 2012.
Paine et al., Dentin sialoprotein and dentin phosphoprotein overexpression during amelogenesis. J Biol Chem. Sep. 9, 2005;280(36):31991-8. Epub Jul. 13, 2005.
U.S. Appl. No. 15/312,047, filed Nov. 17, 2016, Mitsialis et al.
PCT/US2015/031008, dated Dec. 1, 2016, International Preliminary Report on Patentability.

* cited by examiner 1.2% Agarose gel

METHODS AND COMPOSITIONS RELATING TO MESENCHYMAL STEM CELL EXOSOMES

RELATED APPLICATIONS

This application is a national stage filing under 35 U.S.C. 371 of International Application PCT/US2012/028524, filed Mar. 9, 2012, which claims the benefit under 35 U.S.C. § 119(e) of U.S. Provisional Patent Application filed Mar. 11, 2011, entitled "METHODS AND COMPOSITIONS RELATING TO MESENCHYMAL STEM CELL EXOSOMES", Ser. No. 61/451,981, the contents of which are incorporated by reference in their entirety. International Application PCT/US2012/028524 was published under PCT Article 21(2) in English.

FEDERALLY SPONSORED RESEARCH

This invention was made with government support under grant numbers RO1 HL055454 and R01 HL085446 awarded by the National Institutes of Health. The Government has certain rights in this invention.

BACKGROUND OF INVENTION

Premature infants suffer from or at risk of developing certain chronic lung (or respiratory) diseases (or conditions) at higher rates than full term or near term infants. Because the lungs and the breathing capacity of the infant are compromised, these diseases are often fatal. The increased survival rates of premature infants has led to an increased incidence of such lung diseases. Inflammation is a key pathophysiological feature of multiple lung diseases including, pulmonary hypertension (PH or PAH), asthma, chronic obstructive pulmonary disease (COPD), idiopathic pulmonary fibrosis (IPF), and chronic lung disease of infancy, also known as bronchopulmonary dysplasia (BPD). The increased survival rates of premature infants has led to an increased incidence of BPD and its associated complications that include secondary PH, asthma, and increased rehospitalization rate in the first years of life. BPD is a common complication of prematurity (Kinsella et al., Lancet, 2006, 367:1421-1431; Stenmark and Abman, Annu Rev Physiol, 2005, 67:623-661) and in some studies, can affect up to 35-40% of preterm infants born at <29 weeks gestation. Its underlying causes include mechanical injury, oxygen toxicity, infection, and resultant pulmonary inflammation and damage of the developing lung. Attempts to control BPD have involved gentle ventilation strategies and use of anti-inflammatory agents such as corticosteroids. These treatments however have limited success and unacceptable side effects (Baveja and Christou, Semin Perinatol, 2006, 30:209-218). Long-term effects of these chronic lung diseases are also a concern and include sustained lung damage and neurodevelopmental delay. PH is a serious complication of BPD and is associated with high mortality rate. It is also associated with other forms of lung disease such as COPD. More recently, PH has been recognized to be a major complication of schistosomiasis through mechanisms that involve inflammation. Schistosomiasis has very high prevalence in certain parts of the world and is highly linked with secondary PH, potentially dramatically increasing the incidence of this vascular disease worldwide.

SUMMARY OF INVENTION

The invention provides compositions comprising mesenchymal stem cell (MSC) derived exosomes and methods of use thereof in the treatment and/or prevention of lung disease.

In one aspect, the invention provides a composition comprising isolated mesenchymal stem cell (MSC) exosomes formulated for intratracheal administration or administration by inhalation. In one aspect, the invention provides a composition comprising isolated mesenchymal stem cell (MSC) exosomes formulated for intravenous administration.

In another aspect, the invention provides a composition comprising isolated mesenchymal stem cell (MSC) exosomes and a pulmonary surfactant.

In another aspect, the invention provides a composition comprising isolated mesenchymal stem cell (MSC) exosomes and a pulmonary corticosteroid. The pulmonary corticosteroid may be methylprednisolone, although it is not so limited.

In other aspects, the invention provides aerosolized isolated mesenchymal stem cell (MSC) exosomes and compositions comprising aerosolized isolated MSC exosomes.

In another aspect, the invention provides a composition of isolated mesenchymal stem cell (MSC) exosomes for use in the treatment or prevention of lung disease. In another aspect, the invention provides a pharmaceutical composition for use in the treatment or prevention of lung disease comprising isolated mesenchymal stem (MSC) exosomes.

In another aspect, the invention provides a composition of isolated mesenchymal stem cell (MSC) exosomes for use as a medicament to treat or prevent lung disease.

In another aspect, the invention provides a method comprising administering to a subject having or at risk of developing a lung disease an effective amount of isolated mesenchymal stem cell (MSC) exosomes.

In still another aspect, the invention provides use of isolated mesenchymal stem cell (MSC) exosomes to treat or prevent lung disease in a subject, or use of isolated mesenchymal stem cell (MSC) exosomes in the manufacture of a medicament for treating or preventing lung disease In still another aspect, the invention provides isolated mesenchymal stem cell (MSC) exosomes for use in a method for treating or preventing lung disease comprising administering an effective amount of the isolated MSC exosomes to a subject having or at risk of developing lung disease.

In another aspect, the invention provides a method comprising administering to a subject having or at risk of developing a lung disease an effective amount of isolated mesenchymal stem cell (MSC) exosomes.

Various embodiments apply equally to the various aspects of the invention, as described below. In some embodiments, the lung disease is inflammatory lung disease. In some embodiments, the inflammatory lung disease is pulmonary hypertension, asthma, bronchopulmonary dysplasia (BPD), allergy, or idiopathic pulmonary fibrosis. In some embodiments, the lung disease is lung vascular disease. In some embodiments, the lung disease is acute lung injury. In some embodiments, the acute lung injury is associated with sepsis or is ventilator-induced acute respiratory distress syndrome (ARDS).

In some embodiments, the subject has or is likely to develop schistosomiasis.

In some embodiments, the subject is an neonate. In some embodiments, the subject is an infant. In some embodiments, the subject is between 3-18 years of age. In some embodiments, the subject is an adult. In any of these embodiments, the subject may be one that was born prematurely. In some embodiments, the subject was born at less than 35 weeks of gestation. In some embodiments, the subject was born at less than 26 weeks of gestation.

In some embodiments, the isolated MSC exosomes are used together with a secondary agent. In some embodiments, the secondary agent is a steroid, an antioxidant, or inhaled nitric oxide. In some embodiments, the steroid is a corticosteroid. In some embodiments, the corticosteroid is methylprednisolone. In some embodiments, the antioxidant is superoxide dismutase.

In some embodiments, the isolated MSC exosomes are administered within an hour of birth. In some embodiments, the isolated MSC exosomes are administered within 1 month of birth.

In some embodiments, the isolated MSC exosomes are administered intravenously. In some embodiments, the isolated MSC exosomes are administered to lungs or trachea of the subject. In some embodiments, the isolated MSC exosomes are administered by inhalation. In some embodiments, the isolated MSC exosomes are administered in an aerosol. In some embodiments, the isolated MSC exosomes are administered using a nebulizer. In some embodiments, the isolated MSC exosomes are administered using an intratracheal tube.

In some embodiments, the isolated MSC exosomes are administered or formulated with a pulmonary surfactant. In some embodiments, the pulmonary surfactant is isolated naturally occurring surfactant. In some embodiments, the pulmonary surfactant is derived from bovine lung or porcine lung. In some embodiments, the pulmonary surfactant is a synthetic surfactant.

In some embodiments, the isolated MSC exosomes are administered repeatedly to the subject. In some embodiments, the isolated MSC exosomes are administered twice to the subject. In some embodiments, the isolated MSC exosomes are administered continuously to the subject.

In some embodiments, the isolated MSC exosomes are derived from cord blood MSC. In some embodiments, the isolated MSC exosomes are derived from bone marrow MSC.

In some embodiments, the isolated MSC exosomes are autologous to the subject. In some embodiments, the isolated MSC exosomes are allogeneic to the subject.

In some embodiments, the subject is not receiving a cell or organ transplantation.

Thus, in another aspect, the invention provides a pharmaceutical composition comprising an effective amount of isolated human mesenchymal stem cell (MSC) exosomes and a pulmonary surfactant, formulated for delivery to lungs, for use in a human subject having or at risk of developing a lung disease, wherein the subject is less than 4 weeks of age. The invention similarly provides a method of use of the MSC exosomes comprising administering an effective amount of isolated human mesenchymal stem cell (MSC) exosomes and a pulmonary surfactant, formulated for delivery to lungs, to a human subject having or at risk of developing a lung disease, wherein the subject is less than 4 weeks of age. The invention similarly provides use of an effective amount of isolated human mesenchymal stem cell (MSC) exosomes and a pulmonary surfactant, formulated for delivery to lungs, in a human subject having or at risk of developing a lung disease, wherein the subject is less than 4 weeks of age. In some embodiments, the isolated human MSC exosomes are isolated from human umbilical cord (e.g., Wharton's Jelly). In some embodiments, the human subject was born before 37 weeks of gestation. In some embodiments, the human subject has been administered oxygen or has been on a ventilator. In some embodiments, the human subject has or is at risk of developing bronchopulmonary dysplasia. In some embodiments, the bronchopulmonary dysplasia is non-inflammatory. In some embodiments, the isolated human MSC exosomes are administered within 1 day of birth. In some embodiments, the isolated human MSC exosomes are administered within 1 hour of birth.

In another aspect, the invention provides synthetic MSC exosomes having similar or identical characteristics of isolated MSC exosomes, compositions comprising such synthetic MSC exosomes, and methods of their use. The invention contemplates that synthetic MSC exosomes may be formulated and used in the same manner as isolated MSC exosomes. The synthetic exosomes may comprise one, two, three, four, five, six, seven or all eight of the following proteins: haptoglobin (Acc. No. q61646), galectin-3-binding protein (Acc. No. q07797), thrombospondin-2 (Acc. No. q03350), lactadherin (Acc. No. q21956), adipocyte enhancer-binding protein 1 (Acc. No. q640n1), vimentin (Acc. No. p20152), proteasome subunit alpha type 2 (Acc. No. p49722), and amyloid beta A4 protein (Acc. No. p12023). These exosomes may be formulated as described herein for isolated MSC exosomes, including formulated for intranasal or intratracheal administration, or inhalation. They may be formulated and/or administered with pulmonary surfactants or other therapeutic agents.

These and other aspects and embodiments of the invention will be described in greater detail herein.

DETAILED DESCRIPTION OF INVENTION

Figure 1A:
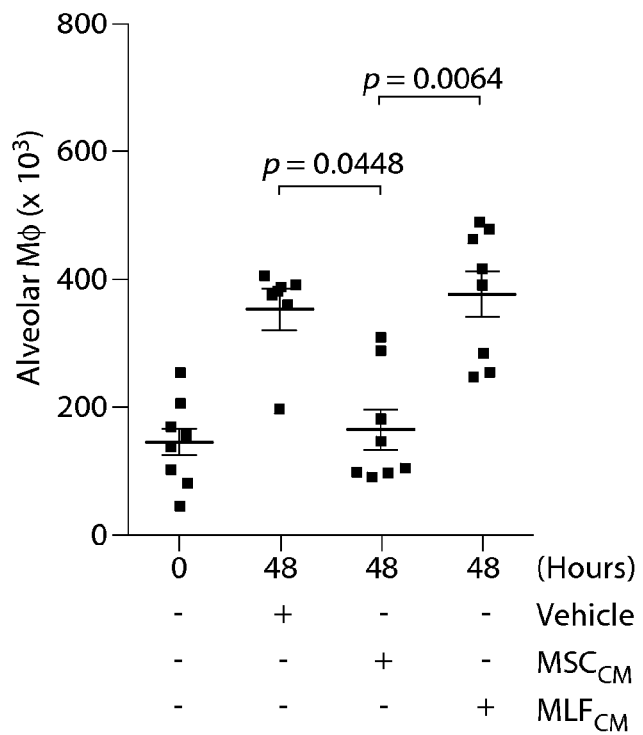
FIG. 1. Secretory factors from BM-MSC are anti-inflammatory. Effects of BM-MSC-CM on hypoxia-induced infiltration of macrophages in the lung (A). Mice (n>8) injected with either vehicle or BM-MSC-CM or MLF-CM were exposed to hypoxia (8.5% $O_2$) for 48 hours and BALFs from the hypoxic mice as well as age-matched normoxic control mice were collected. Number of alveolar macrophages in BALFs were counted by Kimura staining. Comparative immunoblot analysis of proteins in cell-free BALFs from hypoxic and normoxic control mice. (B). Equivalent volume of cell-free BALFs from individual mouse in the same group (n>8) were pooled and proteins from equivalent volume of pooled BALFs were analyzed by western blot using antibodies specific for MCP-1 (top) and HIMF/FIZZ1 (bottom). Relative intensities of MCP-1 and HIMF are represented by normalization over the IgA signal from the same blot.

The invention is based, in part, on the surprising finding that exosomes derived from mesenchymal stem cells provide therapeutic effect to certain lung diseases including but not limited to inflammatory lung diseases.

The invention relates broadly to compositions of mesenchymal stem cell (MSC) derived exosomes, which are interchangeably referred to as mesenchymal stem cell exosomes or MSC exosomes, and methods of their use in the treatment and/or prevention of certain lung diseases including but not limited to inflammatory lung diseases.

Exosomes and Exosome Preparation

The exosomes of the invention are membrane (i.e., lipid bilayer) vesicles that are released from mesenchymal stem cells. They have a diameter ranging from about 30 nm to 100 nm. By electron microscopy, exosomes appear to have a cup-shaped morphology. They sediment at about 100,000×g and have a buoyant density in sucrose of about 1.10 to about 1.21 g/ml. Exosomes may be referred to as microvesicles or nanovesicles.

Exosomes may comprise a number of proteins and/or nucleic acids including RNA species such as miRNA. Proteins that may be expressed in exosomes include Alix, TSG101, CD63, CD9, CD81, moesin, HSP70, Dicer, M-CSF, osteopontin, and one or more of the proteins listed in Table 1 (including any combination of 2, 3, 4, 5, 6, 7, or 8 of those proteins along with any of the proteins listed above). In some embodiments, the exosomes, including the synthetic exosomes discussed below, comprise miRNA, Dicer, M-CSF, osteopontin, and one or more of the proteins of Table 1 (including all of the proteins of Table 1).

Some aspects of the invention refer to isolated exosomes. As used herein, an isolated exosome is one which is physically separated from its natural environment. An isolated exosome may be physically separated, in whole or in part, from tissue or cells with which it naturally exists, including mesenchymal stem cells. In some embodiments of the invention, a composition of isolated exosomes may be free of cells such as mesenchymal stem cells, or it may be free or substantially free of conditioned media. In some embodiments, the isolated exosomes may be provided at a higher concentration than exosomes present in unmanipulated conditioned media.

Exosomes may be isolated from conditioned media from mesenchymal stem cell culture. A method for harvest of exosomes from mesenchymal stem cells is provided in the Examples. Briefly, such method involves first culturing mesenchymal stem cells under standard conditions until they reach about 70% confluency, and then culturing the cells in a serum-free media for 24 hours, following which the conditioned media is collected and subjected to differential centrifugation at 400×g for 10 minutes and 12000×g for 10 minutes in order to remove cells and cellular debris. The clarified conditioned media is then concentrated by ultrafiltration using a 100 kDa MWCO filter (Millipore), and then centrifuged again at 12000×g for 10 minutes. Exosomes are then isolated using size exclusion chromatography by loading the concentrated conditioned media on a PBS-equilibrated Chroma S-200 column (Clontech), eluting with PBS, and collecting fractions of 350-550 microliters. Fractions containing exosomes are identified and potentially pooled. Protein concentration is measured using a standard Bradford assay (Bio-Rad). Aliquots of the enriched exosome preparations can be stored at −80° C.

Exosomes can also be purified by ultracentrifugation of clarified conditioned media at 100,000×g. They can also be purified by ultracentrifugation into a sucrose cushion. GMP methods for exosome purification from dendritic cells have been described in J Immunol Methods. 2002; 270:211-226.

Exosomes can also be purified by differential filtration, through nylon membrane filters of defined pore size. A first filtration though a large pore size will retain cellular fragments and debris. A subsequent filtration through a smaller pore size will retain exosomes and purify them from smaller size contaminants.

Figure 22:
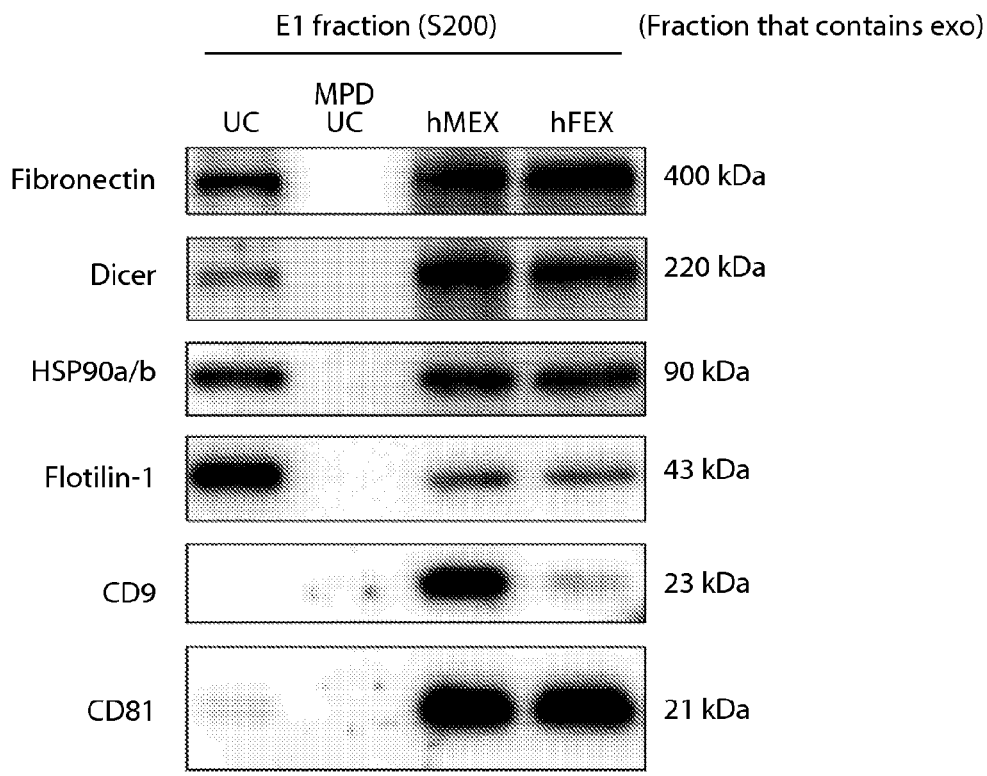
FIG. 22. Markers specific for exosomes from human Wharton's Jelly (WJ) MSCs. Western blot analysis of the 50 nm fraction (E1) from the following sources: UC: unconditioned MSC growth media. MPD UC: microparticle-depleted growth media. Exosomal markers in the growth media are removed by polyethylene glycol precipitation. hMEX: exosomes from WJ MSCs. hFEX: exosomes from human dermal fibroblasts. Tetraspanins CD9 and CD81 are enriched in the exosomal fractions.
Figure 23:
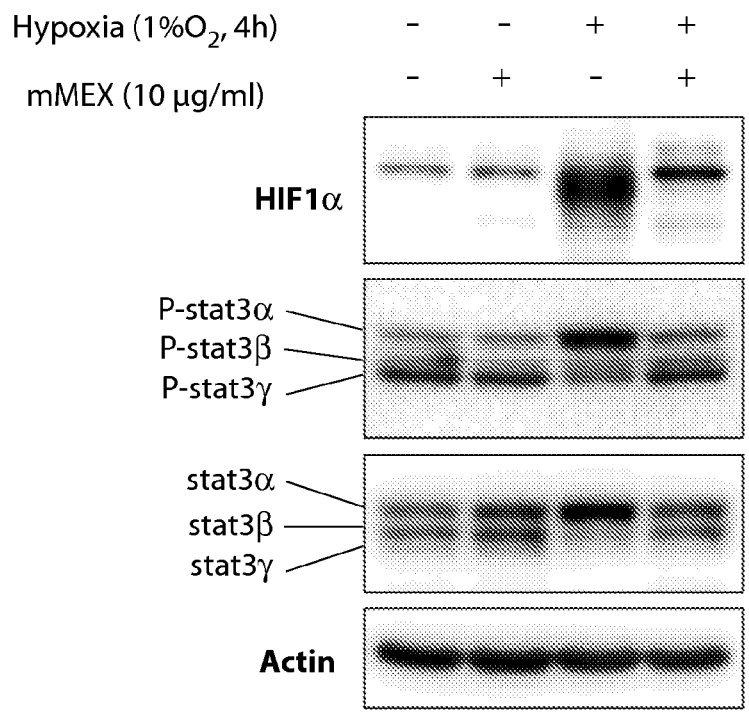
FIG. 23. mMEX suppresses hypoxic upregulation of HIF1a and phosphorylation of STAT3 in mouse lung fibroblasts. Mouse lung fibroblasts were exposed to hypoxia in the presence or absence of mouse bone marrow MSC-derived exosomes (mMEX), as indicated. Hypoxia-inducible factor (HIF) stabilization and STAT3 activation by phosphorylation (P-STAT3) were determined by western blotting.
Figure 24:
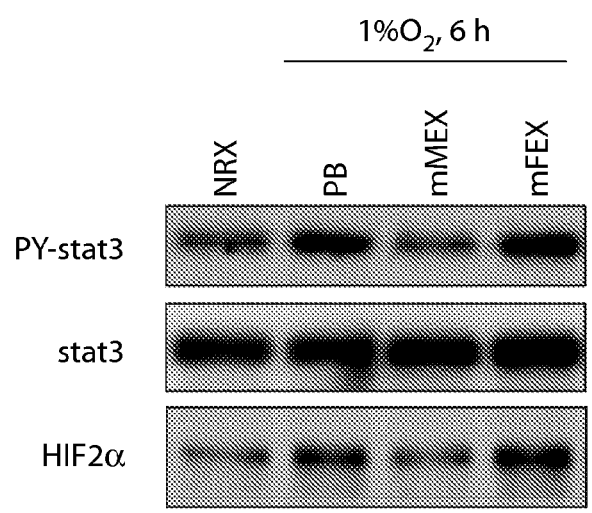
FIG. 24. hPAEC treated with exosomes from mouse bone-marrow derived MSCs (mMEX, 1 ug/ml) or exosomes from mouse lung fibroblasts (mFEX, 1 ug/ml) were exposed to 1% $O_2$ for 6 hrs. Hypoxic activation of STAT3 (P-STAT3), total STAT3 and HIF2a stabilization was determined by western blotting. NRX: normoxia. PBS: hypoxia control.
Figure 25:
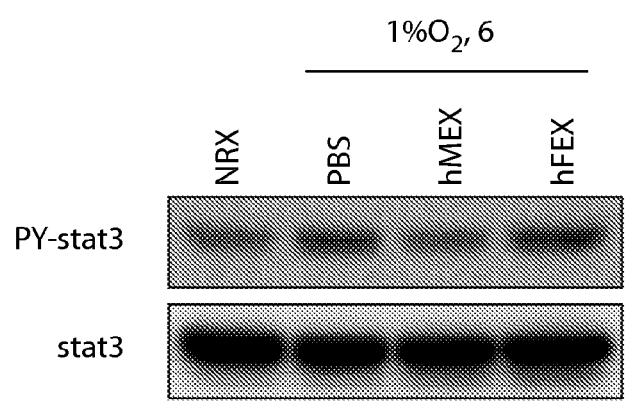
FIG. 25. Human PAECs treated with exosomes from Wharton's Jelly MSCs (hMEX, 1 ug/ml) or exosomes from human dermal fibroblasts (hFEX, 1 ug/ml) were exposed to 1% $O_2$ for 6 hrs. s Stat=3 activation (P-STAT3) and total STAT3 were determined by western blotting. NRX: normoxia. PBS: hypoxia control.

The invention also contemplates the use of synthetic exosomes having some or all the characteristics of the isolated MSC exosomes described herein. These synthetic exosomes would be synthesized in vitro (rather than derived and isolated from MSC or MSC-CM). They may be synthetic liposomes having one or more, including 2, 3, 4, 5, 6, 7, 8 or more of the proteins listed in Table 1 or FIG. 22. They may or may not comprise nucleic acids that encode one or more, including 2, 3, 4, 5, 6, 7, 8 or more of these proteins. Liposome synthesis is known in the art, and liposomes may be purchased from commercial sources. It is to be understood that the various compositions, formulations, methods and uses described herein relating to exosomes derived and isolated from MSC or MSC-CM are also contemplated in the context of synthetic exosomes.

The invention contemplates immediate use of exosomes or alternatively short- and/or long-term storage of exosomes, for example, in a cryopreserved state prior to use. Proteinase inhibitors are typically included in freezing media as they provide exosome integrity during long-term storage. Freezing at −20° C. is not preferable since it is associated with increased loss of exosome activity. Quick freezing at −80° C. is more preferred as it preserves activity. (See for example Kidney International (2006) 69, 1471-1476.) Additives to the freezing media may be used in order to enhance preservation of exosome biological activity. Such additives will be similar to the ones used for cryopreservation of intact cells and may include, but are not limited to DMSO, glycerol and polyethylene glycol.

TABLE 1

Specific and abundant proteins associated with MEX vs. FEX

| Identification | AccNo. | MS/MS spectra | Sequence coverage (%) | MS/MS spectra in FEX |
|---|---|---|---|---|
| Haptoglobin | q61646 | 108 | 15.9 | 2 |
| Galectin-3-binding protein | q07797 | 39 | 43.7 | 0 |
| Thrombospondin-2 | q03350 | 36 | 23.5 | 0 |
| Lactadherin | p21955 | 32 | 26.5 | 2 |
| Adipocyte enhancer-binding protein 1 | q640n1 | 27 | 19.1 | 3 |
| Vimentin | p20152 | 26 | 35.0 | 0 |
| Proteasome subunit alpha type-2 | p49722 | 26 | 50.9 | 3 |
| Amyloid beta A4 protein | p12023 | 26 | 27.1 | 2 |

*Data were presented when total MS/MS hits are >25 and the ratio of MEX/FEX in sequence coverage is >3 for the particular protein.

Mesenchymal Stem Cells

A mesenchymal stem cell is a progenitor cell having the capacity to differentiate into neuronal cells, adipocytes, chondrocytes, osteoblasts, myocytes, cardiac tissue, and other endothelial and epithelial cells. (See for example Wang, Stem Cells 2004; 22(7); 1330-7; McElreavey; 1991 Biochem Soc Trans (1); 29s; Takechi, Placenta 1993 March/April; 14 (2); 235-45; Takechi, 1993; Kobayashi; Early Human Development; 1998; July 10; 51 (3); 223-33; Yen; Stem Cells; 2005; 23 (1) 3-9.) These cells may be defined phenotypically by gene or protein expression. These cells have been characterized to express (and thus be positive for) one or more of CD13, CD29, CD44, CD49a, b, c, e, f, CD51, CD54, CD58, CD71, CD73, CD90, CD102, CD105, CD106, CDw119, CD120a, CD120b, CD123, CD124, CD126, CD127, CD140a, CD166, P75, TGF-bIR, TGF-bIIR, HLA-A, B, C, SSEA-3, SSEA-4, D7 and PD-L1. These cells have also been characterized as not expressing (and thus being negative for) CD3, CD5, CD6, CD9, CD10, CD11a, CD14, CD15, CD18, CD21, CD25, CD31, CD34, CD36, CD38, CD45, CD49d, CD50, CD62E, L, S, CD80, CD86, CD95, CD117, CD133, SSEA-1, and ABO. Thus, mesenchymal stem cells may be characterized phenotypically and/or functionally according to their differentiative potential.

Mesenchymal stem cells may be harvested from a number of sources including but not limited to bone marrow, blood, periosteum, dermis, umbilical cord blood and/or matrix (e.g., Wharton's Jelly), and placenta. Methods for harvest of mesenchymal stem cells are described in greater detail in the Examples. Reference can also be made to U.S. Pat. No. 5,486,359 for other harvest methods that can be used in the present invention.

The mesenchymal stem cells, and thus the exosomes, contemplated for use in the methods of the invention may be derived from the same subject to be treated (and therefore would be referred to as autologous to the subject) or they may be derived from a different subject preferably of the same species (and therefore would be referred to as allogeneic to the subject).

As used herein, it is to be understood that aspects and embodiments of the invention relate to cells as well as cell populations, unless otherwise indicated. Thus, where a cell is recited, it is to be understood that a cell population is also contemplated unless otherwise indicated.

As used herein, an isolated mesenchymal stem cell is a mesenchymal stem cell that has been physically separated from its natural environment, including physical separation from one or more components of its natural environment. Thus, an isolated cell or cell population embraces a cell or a cell population that has been manipulated in vitro or ex vivo. As an example, isolated mesenchymal stem cells may be mesenchymal stem cells that have been physically separated from at least 50%, preferably at least 60%, more preferably at least 70%, and even more preferably a least 80% of the cells in the tissue from which the mesenchymal stem cells are harvested. In some instances, the isolated mesenchymal stem cells are present in a population that is at least 40%, at least 50%, at least 60%, at least 70%, at least 80%, at least 85%, at least 90%, at least 95%, at least 96%, at least 97%, at least 98%, at least 99%, or 100% mesenchymal stem cells as phenotypically and/or functionally defined herein. Preferably the ratio of mesenchymal stem cells to other cells is increased in the isolated preparation as compared to the starting population of cells.

Mesenchymal stem cells can be isolated using methods known in the art, e.g., from bone marrow mononuclear cells, umbilical cord blood, adipose tissue, placental tissue, based on their adherence to tissue culture plastic. For example, mesenchymal stem cells can be isolated from commercially available bone marrow aspirates. Enrichment of mesenchymal stem cells within a population of cells can be achieved using methods known in the art including but not limited to FACS.

Commercially available media may be used for the growth, culture and maintenance of mesenchymal stem cells. Such media include but are not limited to Dulbecco's modified Eagle's medium (DMEM). Components in such media that are useful for the growth, culture and maintenance of mesenchymal stem cells include but are not limited to amino acids, vitamins, a carbon source (natural and non-natural), salts, sugars, plant derived hydrolysates, sodium pyruvate, surfactants, ammonia, lipids, hormones or growth factors, buffers, non-natural amino acids, sugar precursors, indicators, nucleosides and/or nucleotides, butyrate or organics, DMSO, animal derived products, gene inducers, non-natural sugars, regulators of intracellular pH, betaine or osmoprotectant, trace elements, minerals, non-natural vitamins. Additional components that can be used to supplement a commercially available tissue culture medium include, for example, animal serum (e.g., fetal bovine serum (FBS), fetal calf serum (FCS), horse serum (HS)), antibiotics (e.g., including but not limited to, penicillin, streptomycin, neomycin sulfate, amphotericin B, blasticidin, chloramphenicol, amoxicillin, bacitracin, bleomycin, cephalosporin, chlortetracycline, zeocin, and puromycin), and glutamine (e.g., L-glutamine). Mesenchymal stem cell survival and growth also depends on the maintenance of an appropriate aerobic environment, pH, and temperature. Mesenchymal stem cells can be maintained using methods known in the art. (See for example Pittenger et al., Science, 284:143-147 (1999).)

Subjects

The methods of the invention may be performed on any subject likely to derive benefit therefrom, including human subjects, agricultural livestock (e.g., cows, pigs, etc.), prized animals (e.g., horses), companion animals (e.g., dogs, cats, etc.), and the like. In various aspects of the invention, human subjects are preferred. In some aspect, human subjects and human MSC exosomes are used.

The subjects may be those that have a lung disease (or condition) amenable to treatment using the exosomes of the invention, or they may be those that are at risk of developing such a disease (or condition). Such subjects include neonates and particularly neonates born at low gestational age. As used herein, a human neonate refers to an human from the time of birth to about 4 weeks of age. As used herein, a human infant refers to a human from about the age of 4 weeks of age to about 3 years of age. As used herein, low gestational age refers to birth (or delivery) that occurs before a normal gestational term for a given species. In humans, a full gestational term is about 40 weeks and may range from 37 weeks to more than 40 weeks. Low gestational age, in humans, akin to a premature birth is defined as birth that occurs before 37 weeks of gestation. The invention therefore contemplates prevention and/or treatment of subjects born before 37 weeks of gestation, including those born at even shorter gestational terms (e.g., before 36, before 35, before 34, before 33, before 32, before 31, before 30, before 29, before 28, before 27, before 26, or before 25 weeks of gestation). Typically such premature infants will be treated as neonates, however the invention contemplates their treatment even beyond the neonate stage and into childhood and/or adulthood. Certain subjects may have a genetic predisposition to certain forms of lung disease such as for example pulmonary hypertension, and those subjects may also be treated according to the invention.

Methods of Preventing and Treating Diseases

The invention contemplates preventing and treating certain lung diseases. Preventing a disease means reducing the likelihood that the disease manifests itself and/or delaying the onset of the disease. Treating a disease means reducing or eliminating the symptoms of the disease.

The invention intends to prevent and/or treat a number of lung (or pulmonary) diseases. These diseases include inflammatory lung diseases such as but not limited to pulmonary hypertension (PH) which is also referred to as pulmonary artery hypertension (PAH), asthma, bronchopulmonary dysplasia (BPD), allergies, sarcoidosis, and idiopathic pulmonary fibrosis. These diseases also include lung vascular diseases which may not have an inflammatory component. Still other pulmonary conditions that may be treated according to the invention include acute lung injury which may be associated with sepsis or with ventilation. An example of this latter condition is acute respiratory distress syndrome which occurs in older children and adults.

Pulmonary hypertension is a lung disease characterized by blood pressure in the pulmonary artery that is far above normal levels. Symptoms include shortness of breath, chest pain particularly during physical activity, weakness, fatigue, fainting, light headedness particularly during exercise, dizziness, abnormal heart sounds and murmurs, engorgement of the jugular vein, retention of fluid in the abdomen, legs and ankles, and bluish coloring in the nail bed.

Bronchopulmonary dysplasia is a condition that afflicts neonates who have been given oxygen or have been on ventilators, or neonates born prematurely particularly those born very prematurely (e.g., those born before 32 weeks of gestation). It is also referred to as neonatal chronic lung disease. Causes of BPD include mechanical injury for example as a result of ventilation, oxygen toxicity for example as a result of oxygen therapy, and infection. The disease may progress from non-inflammatory to inflammatory with time. Symptoms include bluish skin, chronic cough, rapid breathing, and shortness of breath. Subjects having BPD are more susceptible to infections such as respiratory syncytial virus infection. Subjects having BPD may develop pulmonary hypertension.

Acute respiratory distress syndrome (ARDS), also known as respiratory distress syndrome (RDS) or adult respiratory distress syndrome is a condition that arises as a result of injury to the lungs or acute illness. The injury to the lung may be a result of ventilation, trauma, burns, and/or aspiration. The acute illness may be infectious pneumonia or sepsis. It is considered a severe form of acute lung injury, and it is often fatal. It is characterized by lung inflammation, impaired gas exchange, and release of inflammatory mediators, hypoxemia, and multiple organ failure. ARDS can also be defined as the ratio of arterial partial oxygen tension ($PaO_2$) as a fraction of inspired oxygen ($FiO_2$) below 200 mmHg in the presence of bilateral infiltrates on the chest x-ray. A $PaO_2/FiO_2$ ratio less than 300 mmHg with bilateral infiltrates indicates acute lung injury, which is often a precursor to ARDS. Symptoms of ARDS include shortness of breath, tachypnea, and mental confusion due to low oxygen levels.

Idiopathic pulmonary fibrosis is characterized by scarring or thickening of the lungs without a known cause. It occurs most often in persons 50-70 years of age. Its symptoms include shortness of breath, regular cough (typically a dry cough), chest pain, and decreased activity level.

Prevention and/or treatment may involve in some instances use of the MSC exosomes alone or together with one or more secondary agents. Subjects may also be subjected to mechanical interventions such as ventilation with or without exogenous oxygen administration.

With respect to neonates and particularly low gestation age neonates, the invention contemplates administration of MSC exosomes within 4 weeks, 3 weeks, 2 weeks, 1 week, 6 days, 5 days, 4 days, 3 days, 2 days, 1 day, 12 hours, 6 hours, 3 hours, or 1 hour of birth. In some important instances, the MSC exosomes are administered within 1 hour of birth.

The invention further contemplates administration of MSC exosomes even in the absence of symptoms indicative of a pulmonary disease such as but not limited to BPD.

The invention also contemplates repeated administration of MSC exosomes, including two, three, four, five or more administrations of MSC exosomes. In some instances, the MSC exosomes may be administered continuously. Repeated or continuous administration may occur over a period of several hours (e.g., 1-2, 1-3, 1-6, 1-12, 1-18, or 1-24 hours), several days (e.g., 1-2, 1-3, 1-4, 1-5, 1-6 days, or 1-7 days) or several weeks (e.g., 1-2 weeks, 1-3 weeks, or 1-4 weeks) depending on the severity of the condition being treated. If administration is repeated but not continuous, the time in between administrations may be hours (e.g., 4 hours, 6 hours, or 12 hours), days (e.g., 1 day, 2 days, 3 days, 4 days, 5 days, or 6 days), or weeks (e.g., 1 week, 2 weeks, 3 weeks, or 4 weeks). The time between administrations may be the same or they may differ. As an example, if the symptoms of the disease appear to be worsening the MSC exosomes may be administered more frequently, and then once the symptoms are stabilized or diminishing the MSC exosomes may be administered less frequently.

In some important instances, the MSC exosomes are administered at least once within 24 hours of birth and then at least once more within 1 week of birth. Even more preferably, the MSC exosomes are administered at least once within 1 hour of birth and then at least once more within 3-4 days of birth.

In some instances, repeated intravenous administration of low doses of MSC exosomes may occur. It has been found in accordance with the invention that when low doses of MSC exosomes were administered intravenously to murine subjects, maximal activity was achieved when the MSC exosomes were administered every 2-4 days. In these experiments, 100 ng of MSC exosomes were administered to on average a 20 gram mouse, corresponding to a dose of 5 micrograms per kilogram. When higher doses were used (e.g., 10 micrograms per 20 gram mouse or 0.5 milligrams per kilogram), a single intravenous administration was sufficient to achieve long-term protection. Accordingly, the invention contemplates repeated administration of low dosage forms of MSC exosomes as well as single administrations of high dosage forms of MSC exosomes. Low dosage forms may range from, without limitation, 1-50 micrograms per kilogram, while high dosage forms may range from, without limitation, 51-1000 micrograms per kilogram. It will be understood that, depending on the severity of the disease, the health of the subject, and the route of administration, inter alia, the single or repeated administration of low or high dose MSC exosomes are contemplated by the invention.

Administration, Pharmaceutical Compositions, Effective Amounts

The MSC exosomes may be used (e.g., administered) in pharmaceutically acceptable preparations (or pharmaceutically acceptable compositions), typically when combined with a pharmaceutically acceptable carrier. Such preparations may routinely contain pharmaceutically acceptable concentrations of salt, buffering agents, preservatives, compatible carriers, and may optionally comprise other (i.e., secondary) therapeutic agents.

A pharmaceutically acceptable carrier is a pharmaceutically acceptable material, composition or vehicle, such as a liquid or solid filler, diluent, excipient, solvent or encapsulating material, involved in carrying or transporting a prophylactically or therapeutically active agent. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

Secondary Therapeutic Agents.

The exosomes may be administered with one or more secondary therapeutic agents. As used herein, a therapeutic agent refers to any agent which can be used in the prevention, treatment and/or management of a lung disease such as those discussed herein. These include but are not limited to surfactants, inhaled nitric oxide, almitrine bismesylate, immunomodulators, and antioxidants. Examples of immunomodulators include steroids and corticosteroids such as but not limited to methylprednisolone. Examples of antioxidants include but are not limited to superoxide dismutase.

Certain secondary therapeutic agents used in the treatment or management of certain lung diseases including but not limited to pulmonary hypertension include oxygen, anticoagulants such as warfarin (Coumadin); diuretics such as furosemide (Lasix®) or spironalactone (Aldactone®); calcium channel blockers; potassium such as K-dur®; inotropic agents such as digoxin; vasodilators such as nifedipine (Procardia®) or diltiazem (Cardizem®); endothelin receptor antagonists such as bosentan (Tracleer®) and ambrisentan (Letairis®); prostacyclin analogues such as epoprostenol (Flolan®), treprostinil sodium (Remodulin®, Tyvaso®), and iloprost (Ventavis®); and PDE-5 inhibitors such as sildenafil (Revatio®) and tadalafil (Adcirca®).

Surfactants.

The MSC exosomes may be administered with pulmonary surfactants. A pulmonary surfactant is a lipoprotein mixture useful in keeping lung airways open (e.g., by preventing adhesion of alveolar walls to each other). Pulmonary surfactants may be comprised of phospholipids such as dipalmitoylphosphatidylcholine (DPPC), phosphotidylcholine (PC), phosphotidylglycerol (PG); cholesterol; and proteins such as SP-A, B, C and D. Pulmonary surfactants may be derived from naturally occurring sources such as bovine or porcine lung tissue. Examples include Alveofact™ (from cow lung lavage), Curosurf™ (from minced pig lung), Infasurf™ (from calf lung lavage), and Survanta™ (from minced cow lung, with additional components including DPPC, palmitic acid, and tripalmitin). Pulmonary surfactants may also be synthetic. Examples include Exosurf™ (comprised of DPPC with hexadecanol and tyloxapol), Pumactant™ or Artificial Lung Expanding Compound (ALEC) (comprised of DPPC and PG), KL-4 (comprised of DPPC, palmitoyl-oleoyl phosphatidylglyercol, palmitic acid, and synthetic peptide that mimics SP-B), Venticute™ (comprised of DPPC, PG, palmitic acid, and recombinant SP-C). Pulmonary surfactants may be obtained from commercial suppliers.

Effective Amounts.

The preparations of the invention are administered in effective amounts. An effective amount is that amount of an agent that alone stimulates the desired outcome. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

Administration Route.

The MSC exosomes may be administered by any route that effects delivery to the lungs. Systemic administration routes such as intravenous bolus injection or continuous infusion are suitable. More direct routes such as intranasal administration, intratracheal administration (e.g., via intubation), and inhalation (e.g., via an aerosol through the mouth or nose) are also contemplated by the invention and in some instances may be more appropriate particularly where rapid action is necessary. As used herein, an aerosol is a suspension of liquid dispersed as small particles in a gas, and it includes a fine mist or a spray containing such particles. As used herein, aerosolization is the process of producing of an aerosol by transforming a liquid suspension into small particles or droplets. This may be done using an aerosol delivery system such as a pressurized pack or a nebulizer. Nebulizers include air-jet (i.e., pneumatic), ultrasonic, and vibrating-mesh nebulizers, for example with the use of a suitable propellant such as but not limited to dichlorodifluoromethane, trichlorofluoromethane, dichlorotetrafluoroethane, carbon dioxide or other suitable gas. In addition to nebulizers, other devices for pulmonary delivery include but are not limited to metered dose inhalers (MDIs) and dry powder inhalers (DPIs). Capsules and cartridges of for example gelatin for use in an inhaler or insufflator may be formulated containing lyophilized exosomes and a suitable powder base such as lactose or starch.

The exosomes, when it is desirable to deliver them systemically, may be formulated for parenteral administration by injection, including for example by bolus injection or continuous infusion. Formulations for injection may be presented in unit dosage form, e.g., in ampoules or in multi-dose containers, with or without an added preservative.

The compositions may take such forms as water-soluble suspensions, solutions or emulsions in oily or aqueous vehicles, and may contain formulatory agents such as suspending, stabilizing and/or dispersing agents. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or agents which increase solubility. Alternatively, the exosomes may be in lyophilized or other powder or solid form for constitution with a suitable vehicle, e.g., sterile pyrogen-free water, before use.

It is to be understood that other agents to be administered to subjects being treated according to the invention may be administered by any suitable route including oral administration, intranasal administration, intratracheal administration, inhalation, intravenous administration, etc. Those of ordinary skill in the art will know the customary routes of administration for such secondary agents.

Kits

The invention also encompasses a packaged and labelled pharmaceutical product. This article of manufacture or kit includes the appropriate unit dosage form in an appropriate vessel or container such as a glass vial or plastic ampoule or other container that is hermetically sealed. The unit dosage form should be suitable for pulmonary delivery for example by aerosol. Preferably, the article of manufacture or kit further comprises instructions on how to use including how to administer the pharmaceutical product. The instructions may further contain informational material that advises a medical practitioner, technician or subject on how to appropriately prevent or treat the disease or disorder in question. In other words, the article of manufacture includes instructions indicating or suggesting a dosing regimen for use including but not limited to actual doses, monitoring procedures, and other monitoring information.

As with any pharmaceutical product, the packaging material and container are designed to protect the stability of the product during storage and shipment.

The kits may include MSC exosomes in sterile aqueous suspensions that may be used directly or may be diluted with normal saline for intravenous injection or use in a nebulizer, or dilution or combination with surfactant for intratracheal administration. The kits may therefore also contain the diluent solution or agent, such as saline or surfactant. The kit may also include a pulmonary delivery device such as a nebulizer or disposable components therefore such as the mouthpiece, nosepiece, or mask.

EXAMPLES

Summary

Hypoxia induces an inflammatory response in the lung manifested by alternative activation of macrophages with elevation of pro-inflammatory mediators that are critical for the later development of hypoxic pulmonary hypertension (HPH). Mesenchymal stromal cell (MSC) transplantation prevents lung inflammation, vascular remodeling and right heart failure, and inhibits HPH in experimental models of disease. In this study, we aimed to investigate the paracrine mechanisms by which MSCs are protective in HPH.

We fractionated mouse MSC-conditioned media to identify the biologically-active component affecting in vivo hypoxic signaling and determined that exosomes, secreted membrane microvesicles, suppressed the hypoxic pulmonary influx of macrophages and the induction of pro-inflammatory and pro-proliferative mediators, including monocyte chemoattractant protein-1 and hypoxia-inducible mitogenic factor, in the murine model of HPH. Intravenous delivery of MSC exosomes (MEX) prevented vascular remodeling and development of HPH. Multiple administrations of low dose MEX completely suppressed early hypoxia inflammatory response and ameliorated pulmonary hypertension and right ventricular pathology. A single high dose of MEX was found to be sufficient for preventing vascular remodeling and development of PH induced by chronic hypoxia. In contrast, fibroblast-derived exosomes and MEX-depleted media had no effect. MEX suppressed the hypoxic activation of signal transducers and activators of transcription 3 (STAT3) and the upregulation of the miR-17 superfamily of microRNA clusters, whereas it increased lung levels of miR-204, a key microRNA whose expression is decreased in human PH. MEX produced by human umbilical cord MSCs inhibited STAT3 signaling in isolated human PAECs, demonstrating a direct effect of MEX on hypoxic STAT3 activation.

This study indicates that MEX exert a pleiotropic protective effect on the lung and can prevent PH through suppression of specific STAT3-mediated hyperproliferative pathways induced by hypoxia.

Materials and Methods

Isolation of Bone Marrow-Derived Mesenchymal Stem Cells.

Bone marrow-derived mesenchymal stem cells (BM-MSCs) were isolated from the femurs and tibiae of 5-7 week old FVB/s mice as previously described. Briefly, the ends of each tibia and femur were clipped to expose the marrow and the bones inserted into adapted centrifuge tubes. The tubes were centrifuged for 1 minute at 400×g to collect the marrow. The pellet was resuspended in 3 mL α-minimal essential medium (α-MEM) medium through a 21-gauge needle followed by filtration through a 70-μm nylon mesh filter. The marrow cells were layered on a Ficoll-Paque (Amersham) density gradient, centrifuged and plated. Plastic adherent cells were maintained in culture with media changed every 2-3 days. Following 2-3 passages, immunodepletion was performed as per published protocols and the International Society for Cellular Therapy (ISCT) guidelines[1]. The cells were negatively selected for CD11b, CD14, CD19, CD31, CD34, CD45, and CD79α antigens using the appropriate fluorescent-tagged antibodies (BD Biosciences) in a fluorescence-activated cell sorter (MoFlo), further propagated, and then positively selected for CD73, CD90, CD105, c-kit and Sca-1 antigens, as above. All reagents were purchased from Sigma. Isolated cells between passages 7-12 can be used for the production of conditioned medium and for the isolation of exosomes. Isolated and/or cultured cells may also be cryopreserved prior to production of conditioned medium or exosomes.

Isolation of Primary Mouse Lung Fibroblast.

Primary mouse lung fibroblast (MLF) cultures were derived according to standard methods.

Preparation of MSC-Conditioned Medium (MSC-CM).

Cryo-preserved MSCs were plated with complete medium (αMEM (Invitrogen) supplemented with 10% FBS (Hyclone), 10% Horse serum (Hyclone), and 5 mM L-glutamine (Gibco)) followed by incubation under standard culture conditions. Serum-free MSC-CM produced for 24 hrs from the culture was clarified by differential centrifugation at 400×g for 10 min and 12,000×g for 20 min. Serum-free MSC-CM was concentrated 250 times by ultrafiltration with 100 kDa MWCO filter devices (Millipore) followed by further clarification by centrifugation at 12,000×g for 20 min.

Purification of Exosomes by Sephacryl S-400 Gel Filtration Chromatography.

250× concentrates of MSC-CM was applied on S-400 column (14×300 mm, Pharmacia) pre-equilibrated with PB2XS buffer (20 mM sodium phosphate buffer (pH 7.4) supplemented with 300 mM NaCl) and eluted with constant flow rate (0.4 ml/min). Equivalent volume from each fraction (0.8 ml) was applied on denaturing 10% polyacrylamide gel or native 1.2% agarose gel followed by immuno-staining with specific antibodies against CD81 (Santa Cruz) and SPP-1 (Osteopontin) (R&D Systems). Fractions positive for both CD81 and SPP-1 with higher migration in native agarose gel were pooled and used as an exosome preparation (FIG. 1). Pooled exosomes could be used immediately or snap frozen in liquid nitrogen and then stored at −80° C.

Electron Microscopic Analysis.

Purified exosomes were adsorbed to a carbon coated grid that had been made hydrophilic by a 30 second exposure to a glow discharge. Excess liquid was removed and the exosomes were stained with 0.75% uranyl formate for 30 seconds. After removing the excess uranyl formate, the grids were examined in a JEOL 1200EX Transmission electron microscope and images were recorded with an AMT 2k CCD camera.

Proteomic Analysis of Exosomes.

30 µg of exosomal proteins were separated on 12% denaturing PAGE and subsequently digested with sequencing grade trypsin (Promega). The sequence analysis was performed at the Harvard Microchemistry and Proteomics Analysis Facility by microcapillary reverse-phase HPLC nano-electrospray tandem mass spectrometry (µLC/MS/MS) on a Thermo LTQ-Orbitrap mass spectrometer. The resulting MS/MS spectra of the peptides were then correlated with species specific sequences using the algorithm SEQUEST and programs developed in the Harvard Microchemistry Facility.

Western Blot Analysis.

In experiments for characterizing exosomes, 3 µg proteins from either exosomal fractions or exosome free fraction were separated on 12% polyacrylamide gel electrophoresis following transfer to 0.45 µm PVDF membrane (Millipore). After blocking with 5% skim milk, specific signals were detected using polyclonal goat anti-CD63 (Santa Cruz), anti-CD81 (Santa Cruz), anti-mCSF (R & D systems), anti-osteopontin (R & D systems), polyclonal rabbit anti-moesin (Abcam), anti-14-3-3 family (Abcam), and monoclonal anti-Dicer (Abcam) with appropriate peroxidase-conjugated secondary antibodies. For the control, 35 µg proteins of BM-MSC extract were used in parallel. For analysis of proteins in BALFs, Equivalent volume of cell-free BALF from individual mouse in the same group were pooled then following precipitation overnight by 20% trichloroacetic acid (TCA). The protein pellets resuspended in 1× sodium lauryl sulfate (SDS)-loading buffer were then separated on denaturing tris-tricine polyacrylamide gel. After transfer to 0.2 µm PVDF membranes (Millipore), blots were blocked with 5% skim milk in PBS containing 0.1% tween 20 (Sigma) for 1 hour following incubation with 1:1,000 diluted rabbit polyclonal anti-monocyte chemoattractant protein-1 (MCP-1) antibody (Abcam), anti-hypoxia-induced mitogenic factor (HIMF/FIZZ1/Relmα) antibodies (Abcam), anti-interleukin-10 (Abcam) and anti-interleukin-6 (IL-6) antibodies (Santa Cruz) for overnight at 4° C. To detect mouse immunoglobulin A (IgA) as a loading control, 1:5,000 diluted goat anti-mouse IgA antibody (Abcam) was used. Peroxidase-conjugated anti-rabbit secondary antibody (Santa Cruz) was used in 1:50,000 dilution to visualize immunoreactive bands either by the enhanced chemiluminescence reagent (Pierce) or Lumi-Light$^{PLUS}$ (Roche).

Animals and Hypoxic Exposure.

8-week-old FVB male mice were either obtained from Charles River Laboratories (Wilmington, Mass.) or were raised in the Animal Facility at Children's Hospital Boston. Mice in each group were exposed to 8.5% oxygen in a Plexiglas chamber (Oxycycler, BioSpherix, Redfield, N.Y.) for variable experimental periods. Ventilation was adjusted to remove $CO_2$ so that it did not exceed 5,000 ppm (0.5%) (average range 1,000-3,000 ppm). Ammonia was removed by ventilation and activated charcoal filtration through an air purifier. All animal protocols were approved by the Children's Hospital Animal Care and Use Committee.

Hypoxia-Induced Acute Lung Inflammation Mouse Model.

Mice were injected through left jugular veins with either conditioned medium (40 µg/kg) or exosomes (4 µg/kg) or exosome-free conditioned medium (4 µg/kg). As the control, 50 µl of PBS or culture medium were injected in parallel. 3 hours after injection, mice were continuously exposed to monobaric hypoxia (8.5% $O_2$) for the noted experimental periods. In the time-course experiment, additional injection of MEX was performed on the right jugular veins at 4 days after hypoxic exposure.

Hypoxia-Induced PAH Mouse Model.

Mice injected with exosomes or controls at day 0 and at 4 days after hypoxic exposure were continuously exposed to hypoxia for entire 3 weeks then anesthetized with pentobarbital (50 mg/kg, i.p.). Right ventricular systolic pressure (RVSP) was measured using a closed chest approach and the PowerLab system (ADInstruments, Colorado Springs, Colo.), as previously described[2]. After pressure measurements, lungs were perfused with PBS and inflated with 4% paraformaldehyde to fix the lung architecture. The fixed lungs were then paraffin embedded and sectioned for immunohistochemical analysis. Hearts were immediately analyzed for Fulton's Index measurements (ratio between right ventricular weight and left ventricle plus septum weight, RV/[LV+S]), an assessment of right ventricular hypertrophy.

Bronchoalveolar Lavage and Counting Alveolar Macrophages.

Animals were anesthetized with 2,2,2-Tribromoethanol (250 mg/Kg i.p.) and their trachea were cannulated and blunt ended needle was installed. Bronchoalveolar lavage fluid (BALF) was collected via sequential administration of PBS (0.8 ml, 0.8 ml, 0.8 ml, and 0.9 ml) and approximately 3 ml of individual BALF was recovered. Cells in BALFs were collected by centrifuge at 400×g for 5 minutes and resuspended in Kimura staining solution to selectively count total alveolar macrophages in BALFs.

Immunohistochemical Analysis.

Lung tissue sections were deparaffinized in xylene and rehydrated on slices. Immunohistochemical analysis was performed by incubating with monoclonal anti mouse α-SMA antibody (Sigma) at a dilution of 1:125 overnight at 4° C. after block the tissues for 1 hour. After inactivating endogenous peroxidase with 3% $H_2O_2$ in methanol (Sigma), secondary antibodies, and peroxidase staining was performed according to manufacturer's instructions (Vector laboratories, Burlingame, Calif.). Vessel wall thickness was assessed by measuring α-SMA staining in vessels less than 30 μm in diameter within sections captured under 400× magnification.

Isolation of Human MSCs from Human Umbilical Cord Wharton's Jelly.

Human umbilical cord Wharton's jelly derived MSCs (hUC-MSCs) were isolated according to published methods (Mitchell, K. E. et al., 2003, *Stem Cells* 21:50-60; and Penolazzi, L. et al., 2011, *J Cell Physiol*) with minor modifications. Cord was rinsed twice with cold sterile PBS, cut longitudinally, and arteries and vein were removed. The soft gel tissues were scraped out, finely chopped (2-3 $mm^2$) and directly placed on 100 mm dishes (15 pieces per dish) with DMEM/F12 (1:1) (Invitrogen) supplemented with 10% fetal bovine serum (Hyclone), 2 mM L-glutamine, and penicillin/streptomycin, and incubated for 5 days at 37° C. in a humidified atmosphere of 5% $CO_2$. After removal of tissue and medium, the plates were washed 3 times with PBS, the attached cells were cultured and fresh media replaced 3 times per week. At 70-80% confluence, cells were collected and stained with PE conjugated antibodies for CD34 (Miltenybiotec) and CD45 (Miltenybiotec). Immunodepletion was performed using the anti-PE-microbeads (Miltenybiotec) and MSCS column (Miltenybiotec) according to manufacturer's instructions. The CD34 and CD45 negative populations were further propagated and selected for the expression of MSC markers (CD105, CD90, CD44, and CD73) and the absence of CD11b, CD19, and HLA-DR by using a set of fluorescently-labeled antibodies specific for the characterization of human MSCs (BD Biosciences) using a MoFlo flow cytometry (Beckman Coulter).

Preparation of Conditioned Media.

To exclude contamination from serum-derived microvesicles, serum used for propagation of cell cultures and the collection of conditioned media was clarified by ultracentrifugation at 100,000×g for 18 hrs. MSC were cultured in α-MEM media supplemented with 10% (v/v) fetal bovine serum (FBS, Hyclone) and 10% (v/v) Horse Serum (Hyclone). MLFs were cultured in Dulbecco minimal essential medium (DMEM, Invitrogen) supplemented with 10% FBS and 2 mM L-glutamine (GIBCO). Cultures at 70% confluence were washed twice with PBS and incubated with serum-free media supplemented with 2 mM L-glutamine for 24 hours under standard culture conditions. Conditioned media were collected and cells and debris were removed by differential centrifugations at 400×g for 5 min, at 2,000×g for 10 min, and at 13,000×g for 30 min. The clarified conditioned media were subsequently filtered through a 0.2 μm filter unit and concentrated using a Ultracel-100K (Millipore) centrifugal filter device, to a protein concentration range of 0.1-0.5 mg/ml. Protein levels in the conditioned media were determined by Bradford assay (Bio-Rad).

In Vitro Hypoxia.

Human PAECs were purchased from GIBCO and cultured in M200 medium supplemented with LSGS (Invitrogen). At 80% confluence, cells were exposed to 1% $O_2$ for 5 hours in an inVivo2 workstation (Ruskin Technology, Bridgend, UK) in the presence or absence of exosomal fraction (1 μg/ml), or the exosome-depleted fraction of hUC-MSC conditioned media (1 μg/ml). Cells were lysed and proteins in whole cell lysates were separated on 8% SDS-polyacrylamide gel electrophoresis followed by western blot analysis for phospho-STAT3 and STAT3 (Cell Signaling).

Isolation of Exosomes.

50 μl of concentrated conditioned media was applied on a CHROMA SPIN S-1000 column (Clontech) pre-equilibrated with a buffer containing 20 mM sodium phosphate (pH 7.4) and 300 mM NaCl. Each fraction (0.1 ml) was sequentially collected by gravity. For a large scale preparation, 1.5 ml of clarified and concentrated conditioned media was injected on a column of 16/60 Hiprep Sephacryl S-400 HR pre-equilibrated in the above buffer using an AKTA purifier chromatographic system (GE Healthcare, Piscataway, N.J.). Fractions (1 ml) were collected at a flow rate of 0.5 ml/min. Polystyrene nanospheres of 50 nm diameter (Phosphorex, Fall River, Mass.) were used as a size reference and elution fractions corresponding to this standard's retention volume were pooled and further analyzed.

Protein Extraction and Immunoblotting.

BALF (3 ml) was centrifuged at 420×g for 10 min and cell-free BALF supernatants were used for protein analysis. Equal volumes of BALF specimens from individual animals in the same group were pooled (1 ml) and proteins precipitated overnight by 20% trichloroacetic acid (Sigma). A fraction equivalent to 30% of each protein pellet was dissolved n 1× sodium lauryl sulfate (SDS)-loading buffer was separated on a denaturing 15% polyacrylamide gel. After transfer to 0.2 μm PVDF membranes (Millipore), blots were blocked with 5% skim milk and incubated with 1:1,000 diluted rabbit polyclonal anti-monocyte chemoattractant protein-1 (MCP-1) antibody (Abcam), anti-hypoxia-induced mitogenic factor (HIMF/FIZZ1/Relmα) antibody (Abcam) for overnight at 4° C. To detect mouse Immunoglobulin A, 1:5,000 diluted goat anti-mouse IgA antibody (Abcam) was used. Peroxidase-conjugated anti-rabbit secondary antibody (Santa Cruz) was used in 1:20,000 dilution to visualize immunoreactive bands either by the enhanced chemiluminescence reagent (Pierce) or Lumi-Light$^{PLUS}$ (Roche).

For analysis of proteins from whole lung tissue, frozen lung tissues were chopped for 5 seconds by Polytron in cold PBS containing 2 mM Phenylmethanesulfonyl fluoride (Sigma) and centrifuged at 3,000×g for 3 min. Chopped tissue pellets were washed twice with cold PBS containing 2 mM PMSF by centrifugation at 3,000×g for 3 min each time and the white cleaned tissue pieces were subjected on the lysis with RIPA buffer containing protease inhibitor cocktail (Roche) and phosphatase inhibitor cocktail (Thermo). 40 μg of lung tissue extracts were separated on 10-20% gradient gel (Invitrogen). Antibodies used in immunoblotting were against MCP-1, HIMF, IL-6, vascular endothelial growth factor (Abcam), total STAT3, and phospho-STAT3 (Y705) (Cell Signaling). For loading control, mouse monoclonal β-actin antibody (Sigma) was used.

Exosome preparations were separated on 12% polyacrylamide gel and then transferred onto 0.45 μm PVDF membrane (Millipore). Goat polyclonal anti-CD63 (1:1,000; Santa Cruz) antibody, polyclonal rabbit anti-CD81 (1:1,000, Santa Cruz), and monoclonal anti-Dicer (1:1,000, Abcam) were used. To visualize the specific protein bands, same ECL reagents described above were used. The ImageJ program from NIH was used for quantitation through densitometric analysis after appropriate background subtraction.

Quantification of microRNAs.

Total lung RNA was extracted by the method of Chomczynski & Sacchi (1987 *Anal Biochem* 162:156-159) and 750 ng was used as a template for reverse transcriptase with specific primers for each target microRNA (TaqMan Reverse Transcription Kit, Applied Biosystems, Foster City, Calif.). Each reverse transcription reaction included also the primer for the small nuclear RNA sno202, which was used as an internal control. 37.5 ng cDNA was used for each 20 µl qPCR reaction with TaqMan universal master mix II with no UNG (Applied Biosystems) in the presence of probes specific for the indicated microRNAs and the internal control (TaqMan microRNA assay, Applied Biosystems). Amplification was performed at 50° C. for 2 min, 95° C. for 10 min, followed by 40 cycles of 95° C. for 15 sec, 60° C. for 1 min, on a StepOne Plus platform (Applied Biosystems).

Results

BM-MSC Secrete Factors that Suppress Hypoxia-Induced Acute Inflammatory Responses.

Figure 1B:
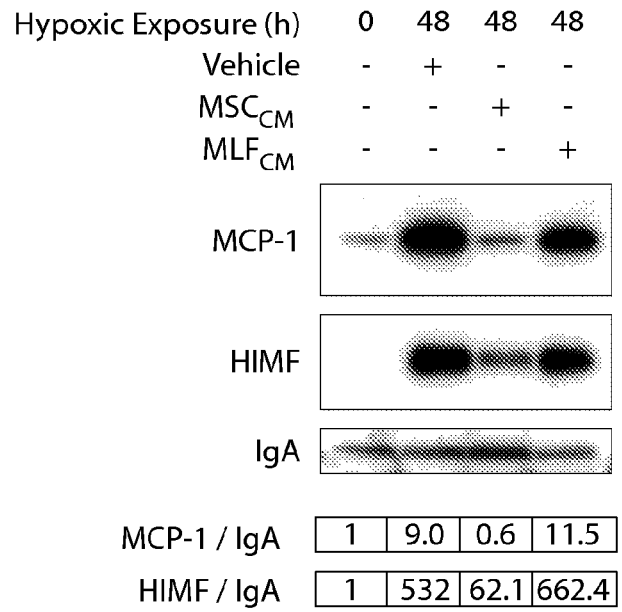

Therapeutic capacity of BM-MSCs have been observed from several animal models of lung injuries. We first determined BM-MSCs were relevant to hypoxia-induced pulmonary inflammation by their paracrine manner. Hypoxic exposure results in significant pulmonary accumulation of macrophages and elevation of proinflammatory mediators within 2 days[2]. To test paracrine potentials of BM-MSCs on this animal model, mice receiving either BM-MSC-conditioned medium (BM-MSC-CM) or vehicle or MLF-conditioned medium (MLF-CM) were exposed to monobaric hypoxia for 2 days. Consequently, hypoxia-derived acute pulmonary influx of macrophages was blocked by BM-MSC-CM treatment while mice injected with vehicle or MLF-CM showed a significant accumulation of macrophages in lung (FIG. 1A), suggesting BM-MSCs secrete factor(s) suppress hypoxia-derived lung inflammatory responses which signal to recruit macrophages into the lung. As it has been observed that hypoxic conditioning upregulates pulmonary levels of proinflammatory mediators, cell-free BALFs from the mice were applied to comparative analysis for hypoxia-responsible proinflammatory mediators, MCP-1 and HIMF/FIZZ1. In vehicle or MLF-CM injected mice, secretion levels of both MCP-1 and HIMF in the lung were significantly increased by hypoxic exposure for 48 hours. In contrast, the elevation of these mediators by hypoxia was effectively suppressed in BM-MSC-CM treated mice (FIG. 1B). Taken together, secretory factor(s) of BM-MSCs are anti-inflammatory agents which prevent pulmonary recruitment of macrophages via blocking the hypoxia-induced upregulation of MCP-1 and HIMF/FIZZ1 in the lung.

BM-MSC Secrete Exosomes.

Figure 2:
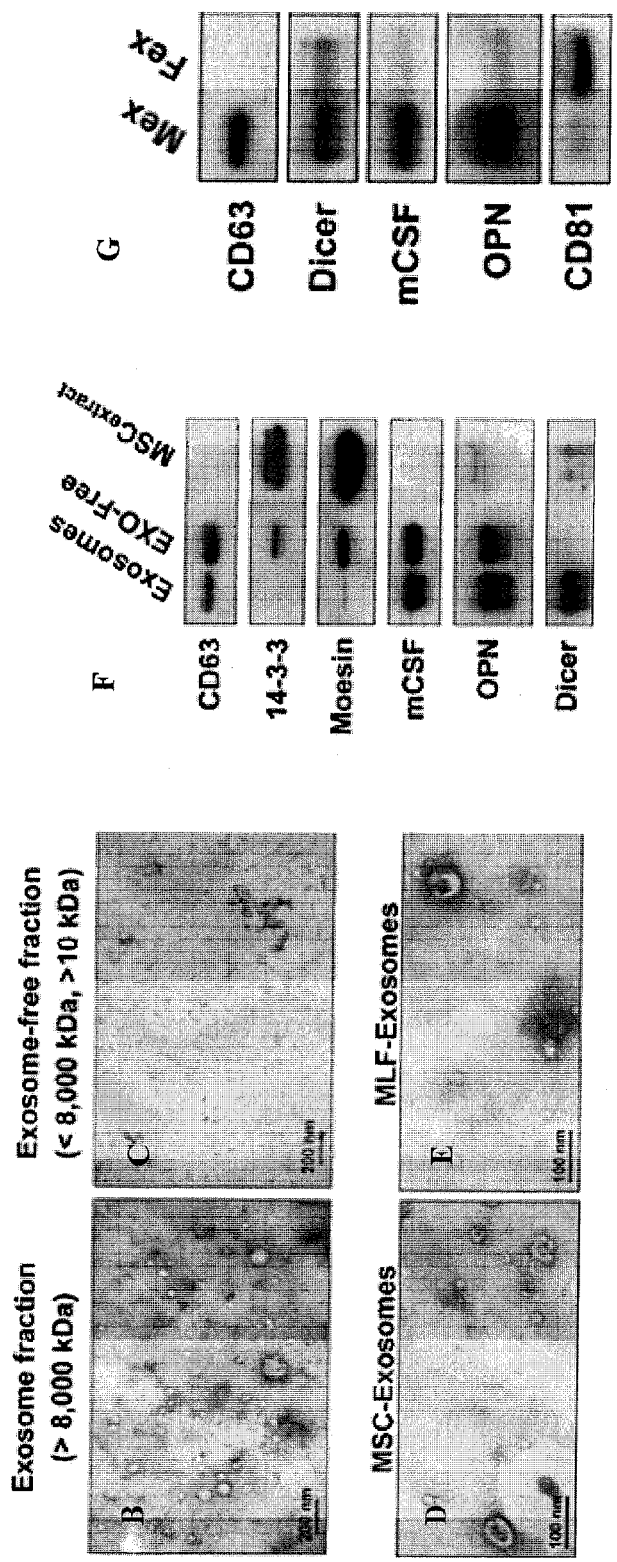
FIG. 2. Isolation of exosomes from cell-free BM-MSC-conditioned medium. Exosomes in BM-MSC-CM or MLF-CM were isolated by ultrafiltration and size-exclusion chromatography. 1.6% (w/w) of proteins in BM-MSC-CM were associated with exosomes and exosomes in the fractions from size-exclusion chromatography were visualized by electron microscopy (B-E). To verify the isolation of exosomes from BM-MSC-CM, the fraction at void volume ($v_e=v_o$) (B) and the fraction between void volume and total volume ($v_o<v_e<v_t$) of the column (C) were analyzed by negative staining electron microscopy at 30,000 magnification. Morphology and size distribution of exosomes isolated from BM-MSC-CM (D) or MLF-CM (E) were identical. Western blot analysis against proteins associated with exosomes (F-G). 3 μg proteins in each sample were assayed in western blot using the antibodies against CD63, 14-3-3s, moesin, macrophage colony stimulating factor (mCSF), osteopontin (OPN), and dicer. For positive control, 35 ug proteins of BM-MSC whole cell lysates were used.

We isolated small vesicles in BM-MSC-CM by a procedure including ultrafiltration and size-exclusion chromatography. Table 2 shows the degree of enrichment achieved in these experiments. As summarized in FIG. 2, approximately 1.6% (w/w) of secretory proteins in BM-MSC-CM might be associated with their exosomes. MLF-derived exosomes (FEX) were isolated as a control and analyzed in parallel. From the electron microscopic analysis, exosomes were observed only in the fraction within void volume of the column, suggesting that size exclusion chromatography to exclude molecules smaller than 8,000 kDa is highly selective to enrich exosomes (FIGS. 2B, 2C). Moreover, electron micrographs of exosomes from the equivalent fraction of BM-MSC-CM and MLF-CM confirmed that exosomes shed from the both types of cells demonstrated physical parameters of typical exosomes such as heterogeneity in diameter ranging from 30 to 100 nm and biconcave morphological characteristics (FIG. 2D, 2E). With regard to protein content of BM-MSC-derived exosomes (MEX), western blot analyses showed that MEX were positive for typical exosomal proteins such as CD63 and moesin, and also highly associated with immunomodulatory proteins including monocyte colony stimulating factor (mCSF) and osteopontin (OPN/SPP1). Some isoforms of 14-3-3 family, which are small polypeptides with a molecular mass of approximately 30 kDa capable of binding numerous functionally diverse signaling proteins, co-purified with exosomes indicating that a certain subset of 14-3-3 isoforms is associated with MEX. Moreover, Dicer which catalyzes a critical processing step of microRNA maturation in cytoplasm was only detected in the exosomal fraction, strongly supporting that microRNAs are another constituent of exosomes. It is interesting to note that mCSF and OPN as well as CD63 and moesin were also abundantly detected in exosome-free fractions obtained during the purification procedure, suggesting the presence of their soluble isoforms in the exosome-free fraction or weak or low affinity association with the surface of exosomes (FIG. 2F). Comparative western analysis revealed that MEX are highly enriched in CD63, Dicer, mCSF, and osteopontin as compared to FEX while CD81 is more abundant in FEX (FIG. 2G). Consequently, MEX preserve physical characteristics of typical exosomes in terms of size and morphology and were highly enriched with Dicer and immune modulators compared with FEX. We further performed comparative proteomic analyses between the exosomes from the two different cell types by mass spectrometry to further investigate the physiological roles of MEX.

Anti-Inflammatory Roles of BM-MSCs were Mediated by their Secretory Exosomes.

Figure 3A:
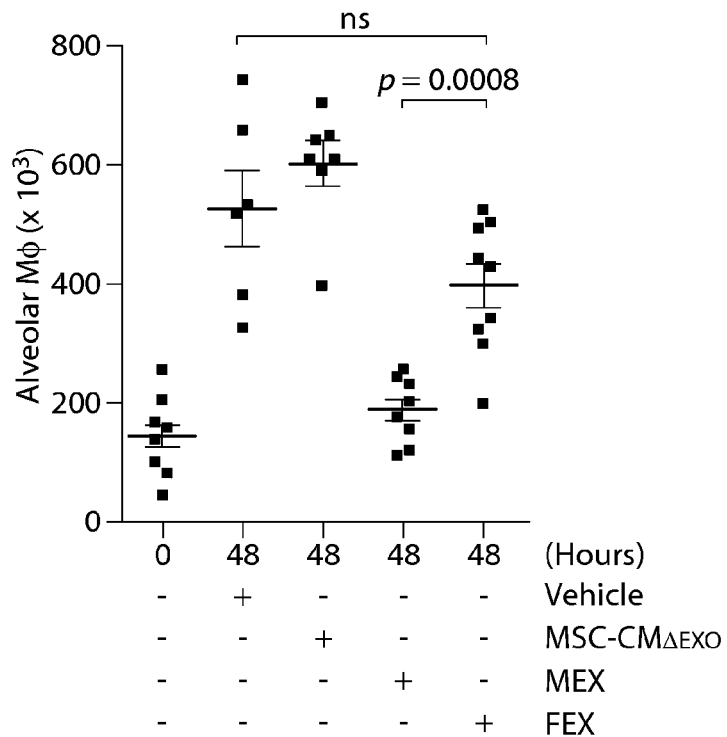
FIG. 3. MEX suppress hypoxia-induced acute pulmonary inflammation. Mice (n>7) injected with either vehicle or MEX or exosome-free fraction of BM-MSC-CM or FEX were exposed to hypoxia (8.5% $O_2$) for 48 hours and BALFs of the hypoxic mice and age-matched normoxic mice were collected. Number of alveolar macrophages in BALF from each mouse was counted by Kimura staining (A). Comparative immunoblot analysis of proteins in cell-free BALFs from hypoxic and the normoxic control mice (B). Equivalent volume of cell-free BALFs from individual mouse in the same group (n>7) were pooled and proteins from equivalent volume of pooled BALFs were analyzed by western blot using antibodies specific for MCP-1 (top) and HIMF/FIZZ1 (bottom). Relative levels of MCP-1 and HIMF are represented by normalization over the IgA signal from the same blot.
Figure 3B:
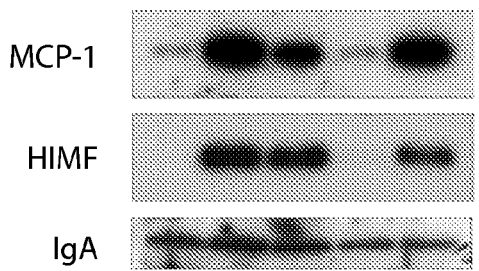

We further investigated whether BM-MSC-derived exosomes are physiologically functional in the experimental model of hypoxia-induced acute pulmonary inflammation. Mice injected with purified MEX were exposed to monobaric hypoxia of 8.5% $O_2$. After continuous exposure to hypoxia for 48 hours, we observed that hypoxia-derived pulmonary influx of macrophages was effectively prevented by administration of MEX. In contrast, FEX or exosome-free fraction of BM-MSC-CM failed to prevent the pulmonary influx of macrophages (FIG. 3A). Total proteins from cell-free BALFs were studied using immunoblot analysis. Upregulation of secretory proinflammatory mediators such as MCP-1 and HIMF/FIZZ-1 by hypoxia were completely abrogated by administration of MEX, while these were not blocked by injection of vehicle or FEX (FIG. 3B). Interestingly, exosome-free fraction of BM-MSC-CM failed to suppress hypoxia-induced upregulation of these proinflammatory mediators. There were few other differences in protein contents between the exosomal fraction and exosome free fraction, suggesting the possibility that nucleic acids in exosomes may be important in the response. These data highlight that BM-MSC-derived secretory factors specifically localized on exosomes effectively suppress hypoxia-induced pulmonary inflammatory responses by blocking the hypoxia-derived signal to upregulate proinflammatory mediators MCP-1 and HIMF/FIZZ1.

Administration of MEX Abrogates Hypoxia-Induced Lung Inflammatory Responses.

Figure 4A:
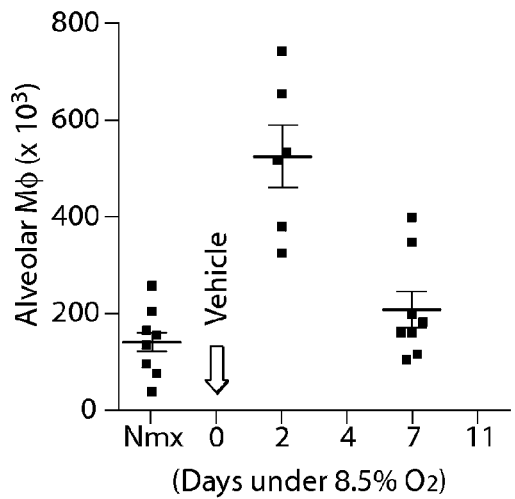
FIG. 4. Time course effect on hypoxia-derived pulmonary inflammation by single and multiple administration of MEX. Mice injected with either vehicle (A) or MEX (B) at day 0 were exposed to hypoxia (8.5% $O_2$) for the indicated periods. For multiple injection experiment, mice received MEX at day 0 were exposed to hypoxia for 4 days. Second injection of the same dose of MEX at day 4 were followed by additional exposure to hypoxia for the days indicated (C). BALFs were collected at selected time periods of hypoxic conditioning and the number of alveolar macrophages in BALF from individual mouse were counted. Equivalent volume from cell-free BALFs of individual mouse in the same group (n>7) were pooled and proteins from 10% (v/v) of pooled BALFs were analyzed by western blot using antibodies specific for MCP-1 and HIMF (D).
Figure 4B:
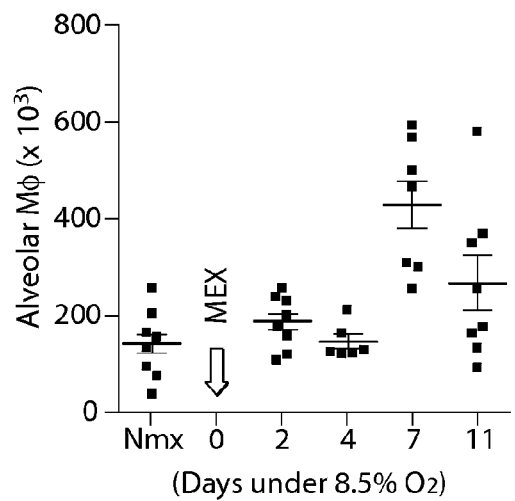
Figure 4C:
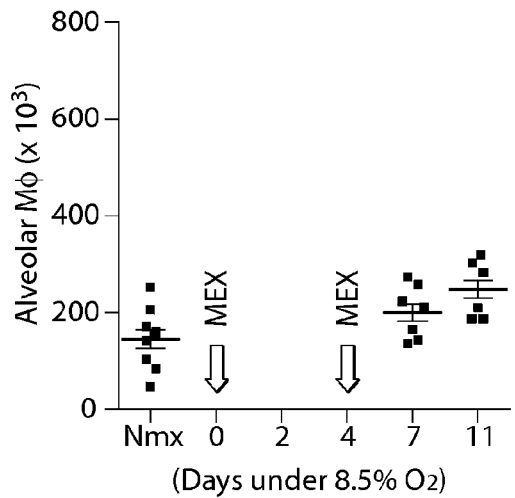
Figure 4D:
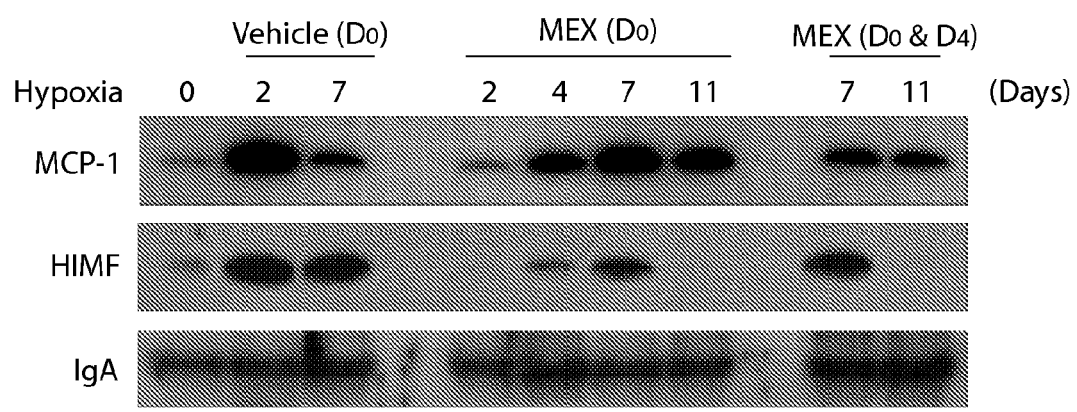

We observed that BM-MSC secrete exosomes which abrogate hypoxic signals to recruit macrophages into the lung, and also observed that hypoxic exposure leads to acute inflammatory responses in the lung within 2 days. We further investigated the time course of single or multiple treatments of MEX on pulmonary inflammatory responses until 7 to 11 days of hypoxic exposure. In vehicle injected group, mice exhibited acute pulmonary influx of macrophages and dramatic elevation of pulmonary level of both MCP-1 and HIMF/FIZZ1 by 2 days of hypoxic exposure with the inflammatory peak resolving at 7 days of hypoxic exposure. Unlike with reductive number of alveolar macrophages and pulmonary level of MCP-1, high level of HIMF/FIZZ1 was sustained for 7 days of continuous hypoxic exposure, suggesting MCP-1 is mainly regulating pulmonary influx of macrophages while HIMF/FIZZ1 might play distinct roles in the response to hypoxia (FIGS. 4A, 4D). Importantly, a single injection of MEX was not able to suppress hypoxia-induced inflammatory responses more than 4 days under hypoxia, so hypoxia-responsible pulmonary inflammation was initiated after 4 days of injection and peaked at 7 days then resolved at 11 days (FIGS. 4B, 4D). More importantly, additional injection of MEX at the $4^{th}$ day of hypoxic exposure sustained the blockade of pulmonary inflammation under hypoxia up to 11 days (FIG. 4C). With regard to HIMF/FIZZ1 regulation by MEX, a single injection of MEX is able to suppress hypoxia-induced upregulation of HIMF/FIZZ1 for 4 days of hypoxia. Additional injections of MEX were not able to abrogate upregulation of HIMF/FIZZ1 at 7 days of hypoxia, suggesting other temporal regulatory pathway might be involved in this response. Taken together, hypoxia-induced acute pulmonary inflammation was temporally suppressed by a single injection of MEX and the anti-inflammatory effects able to neutralize pulmonary response to hypoxia were maintained by sequential and multiple administration.

Hypoxia-Induced PAH Suppressed by BM-MSC-Derived Exosomes.

Figure 5A:
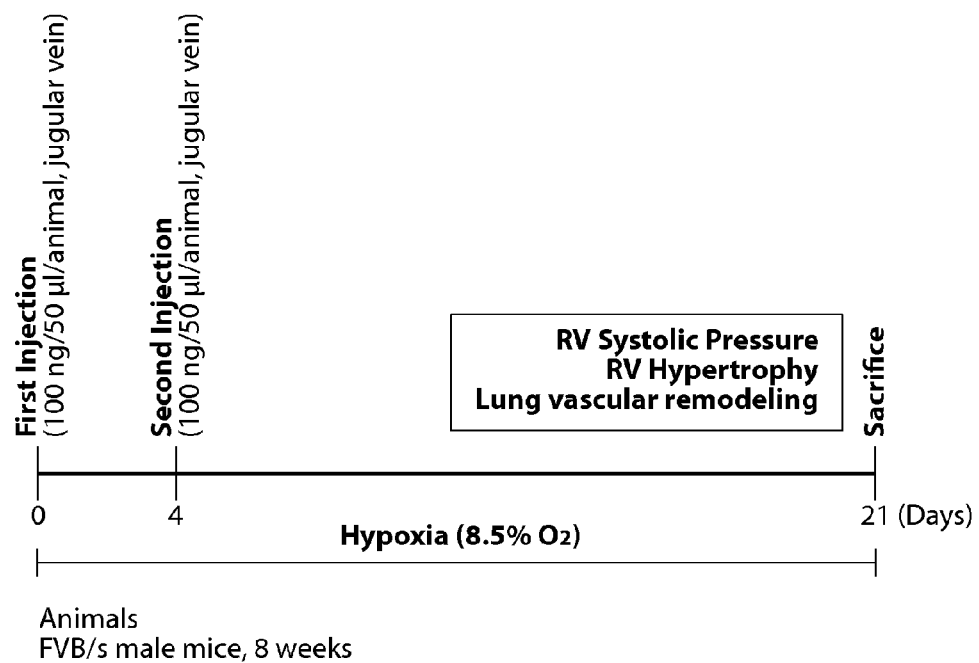
FIG. 5. MEX suppress hypoxia-induced PAH. Mice (n>7) were injected once or twice with either vehicle (at day 0 and day 4) or MEX (at day 0 and/or day 4), or FEX (at day 0 and day 4) were exposed to hypoxia (8.5% O2) for 3 week periods (A). RVSP (B) and Fulton's Index (C) of the hypoxic and normoxic control mice were measured at the end of experimental period. Paraffin embedded lung sections from randomly selected mice (n=4) in each group were immunostained for α-SMA to highlight pulmonary arterioles vessel walls (D). Original magnification for images: 400×. Small pulmonary arterioles with 20~30 μm in diameter from each group were selected to measure vessel wall thickness which was expressed as a percentage of total vessel area (E). Data are expressed as mean±SEM (n=40~50 arterioles per group).
Figure 5B:
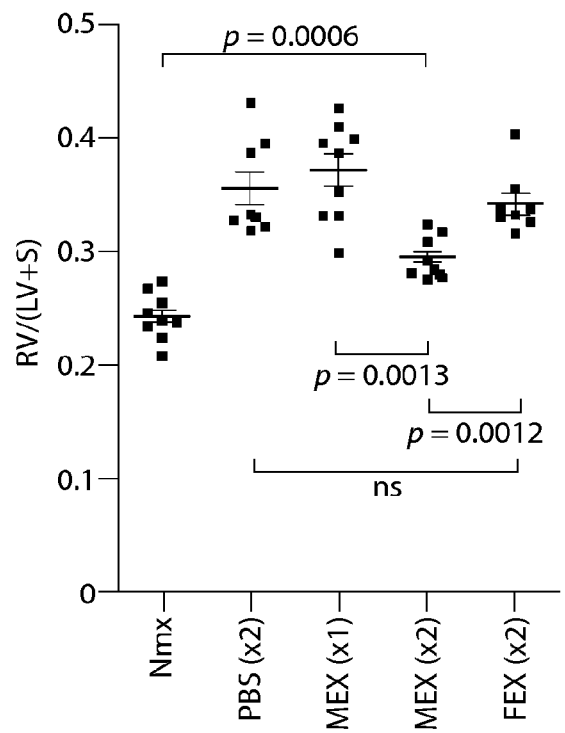
Figure 5C:
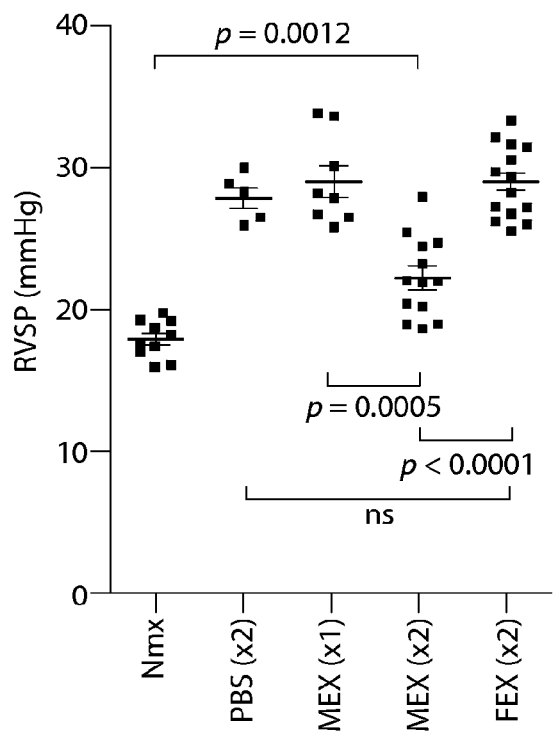
Figure 5D:
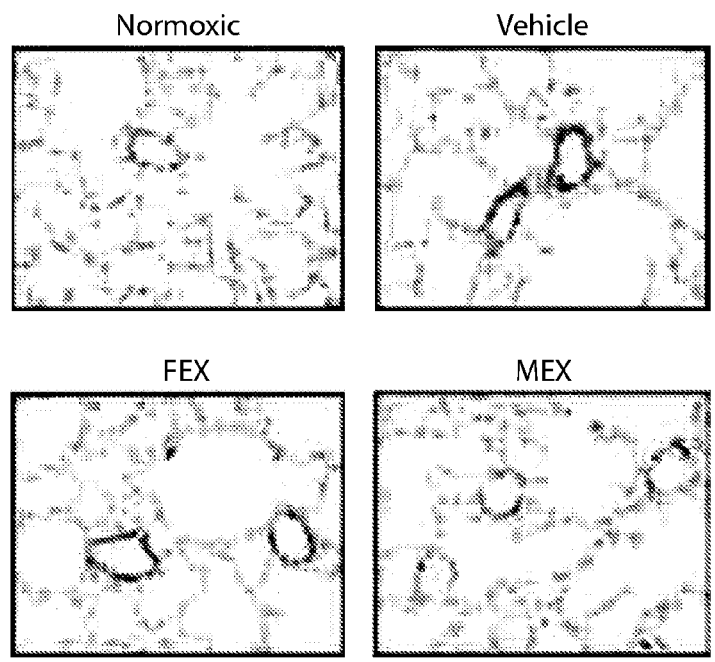
Figure 5E:
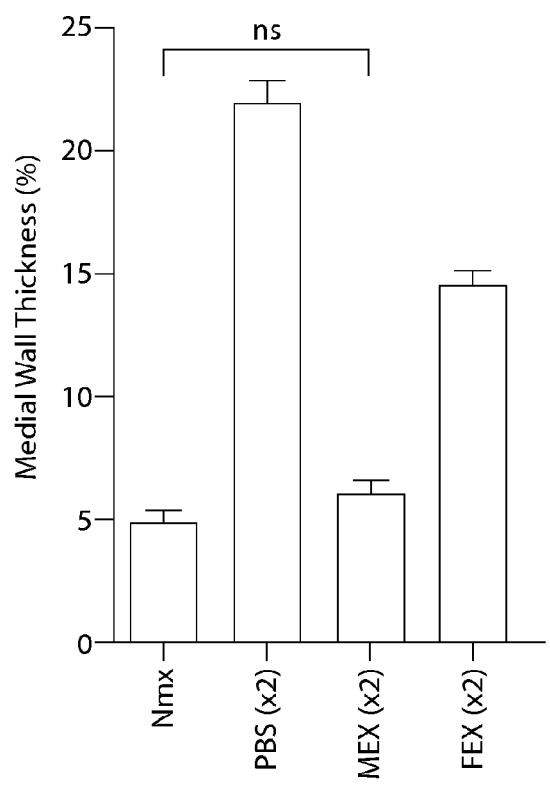
Figure 6A:
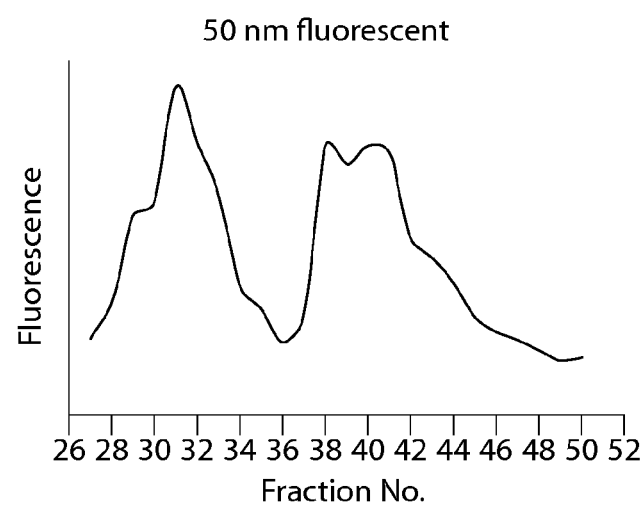
FIG. 6. Purification of MSCs-derived exosomes. Exosomes were purified by Sephacryl S-400 gel filtration column chromatography. Negatively charged fluorescent 50 nm nanoparticles applied on the S-400 column and eluted with identical condition to the exosome purification (A). From exosome purification, equivalent volume of each fraction was separated on both 10% denaturing polyacrylamide gel (B) and 1.2% agarose gel electrophoresis (C). Blot for the agarose gel was stained with anti-CD81 antibody (D).
Figure 6B:
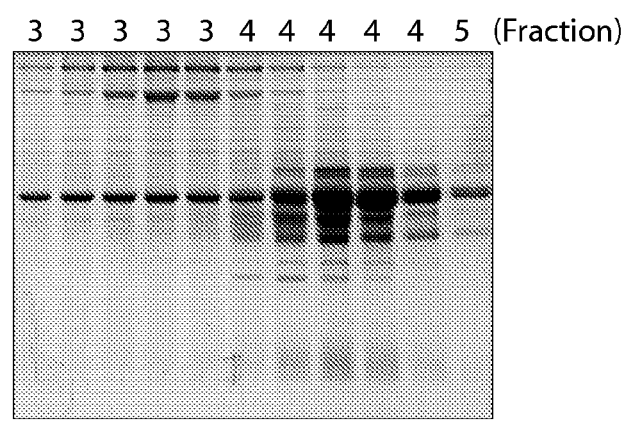
Figure 6C:
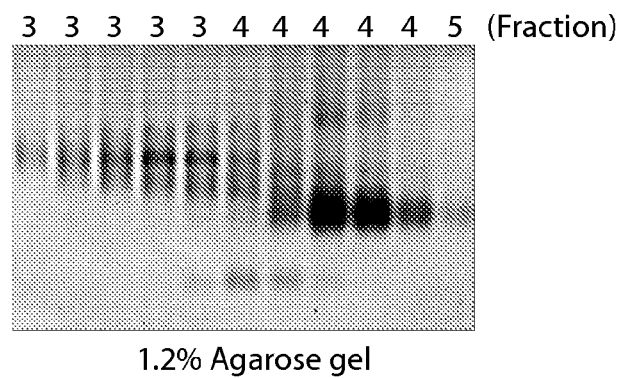
Figure 6D:
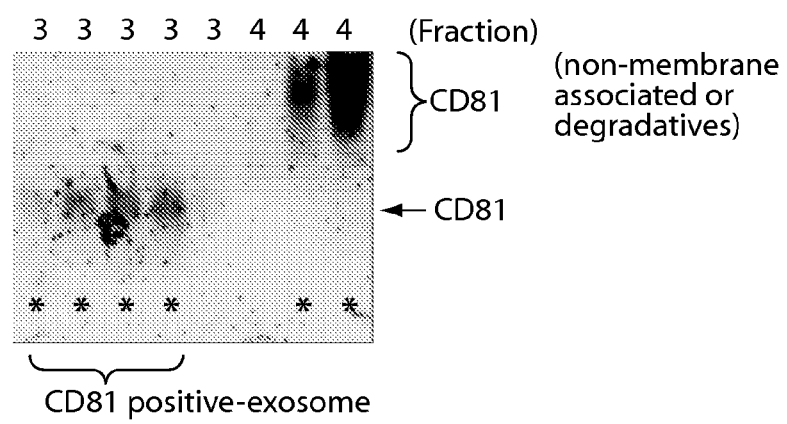
Figure 7A:
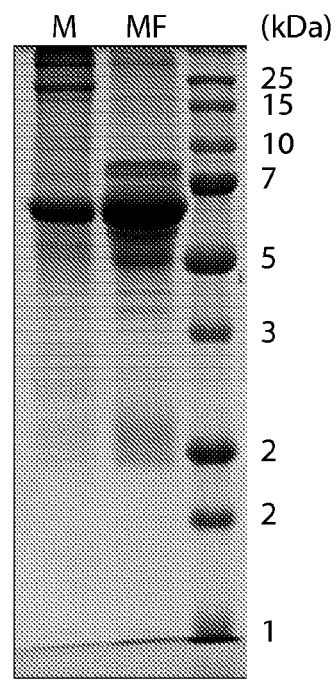
FIG. 7. Comparative biochemical analysis of MSC-derived exosomes and exosome-free fractions. Equivalent protein quantities in both pools of exosome fractions (M) and exosome-free fractions (MF) were separated on denaturing 12% polyacrylamide gel (A). 1.2% agarose gel loaded by equivalent protein quantities in both pools of exosome fractions and exosome-free fractions as well as 50 nm nanoparticles in the absence (left, B) or presence of 0.5% SDS (right, B) were stained with colloidal blue. 1.2% agarose gel loaded by equivalent protein quantities in both pools of exosome fractions and exosome-free fractions were stained with ethidium bromide for nucleic acids (left, C) or colloidal blue for proteins (right, C). Blots for gels loaded with equivalent protein quantities in both pools of exosome fractions and exosome-free fractions separated on both 1.2% agarose gel and 12% denaturing polyacrylamide gel were immunostained with anti-CD81 and anti-SPP-1 antibodies (D). M, Pool of exosomal fractions; MF, Pool of exosome-free fractions; N, negatively charged fluorescent 50 nm nanospheres.
Figure 7B:
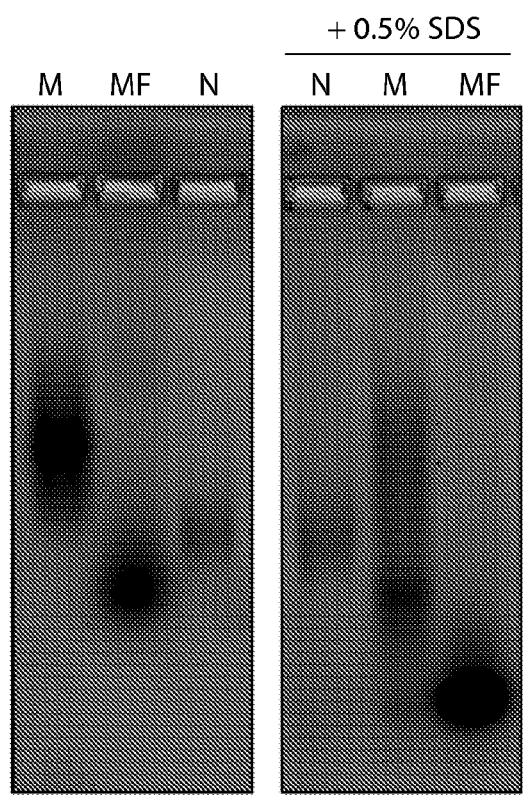
Figure 7C:
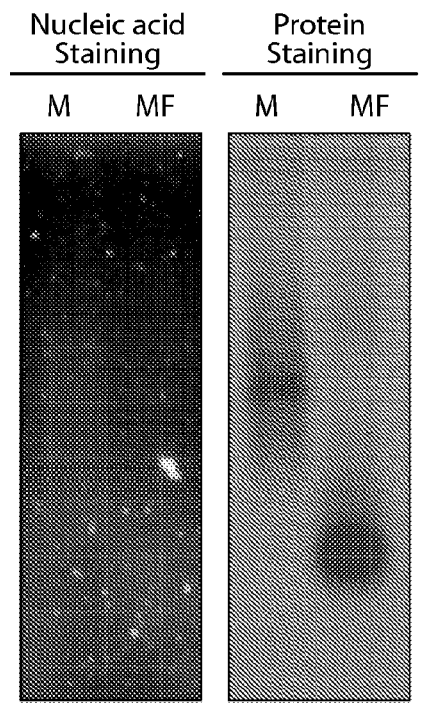
Figure 7D:
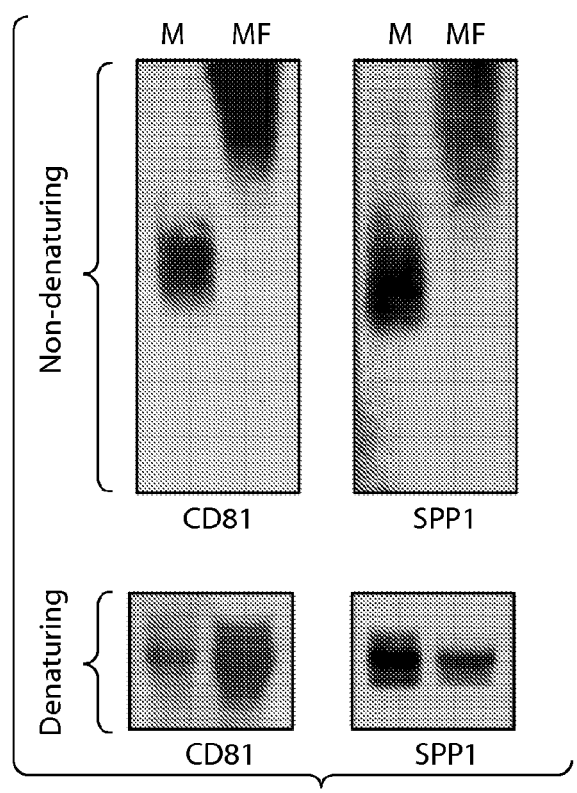
Figure 8A:
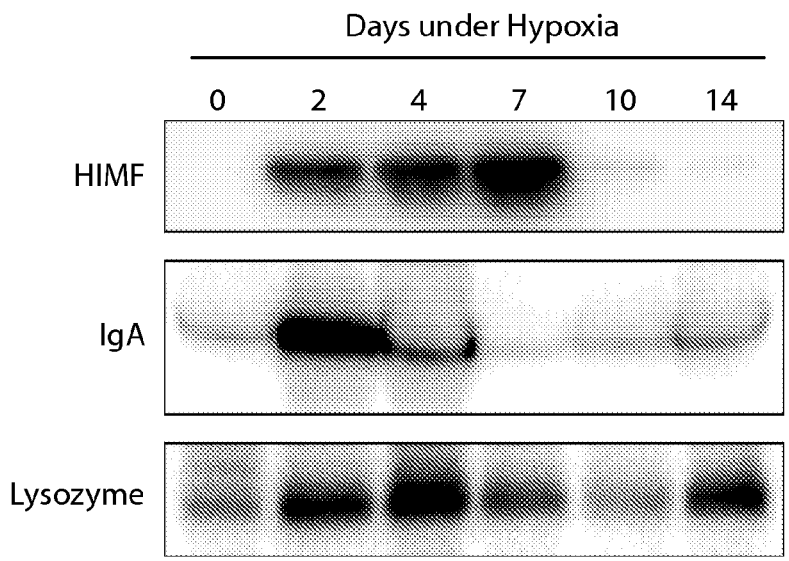
FIG. 8. Hypoxia-induced secretion of HIMF/FIZZ-1/Retnlα in the lung. Mice were exposed over indicated time periods to monobaric hypoxia (8.5% $O_2$). Proteins in BAL normalized by volume (A) and quantity (B) from each individual mouse in the same group were pooled and separated on 14% polyacrylamide gel. Levels of HIMF, lysozyme, and IgA were evaluated by western blot analysis using specific antibodies.
Figure 8B:
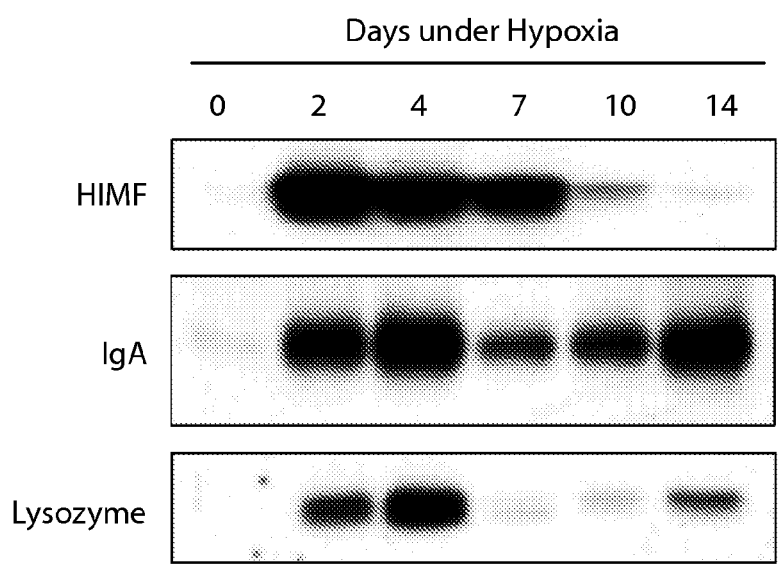
Figure 9A:
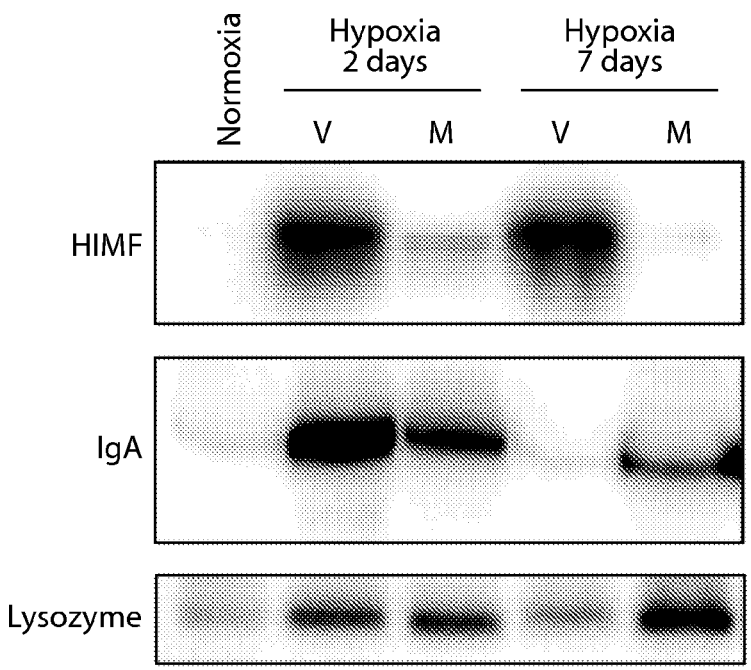
FIG. 9. MSCs-derived exosomes suppress hypoxia-induced secretion of HIMF/FIZZ-1/Retnlα in the lung. Mice injected either with 10 μg of MEX (M) or vehicle (V) by tail vein were exposed over indicated time periods to monobaric hypoxia (8.5% $O_2$). Proteins in BAL normalized by volume (A) and quantity (B) from each individual mouse in the same group were pooled and separated on 14% polyacrylamide gel electrophoresis. Levels of HIMF, lysozyme, and IgA were evaluated by western blot analysis using specific antibodies.
Figure 9B:
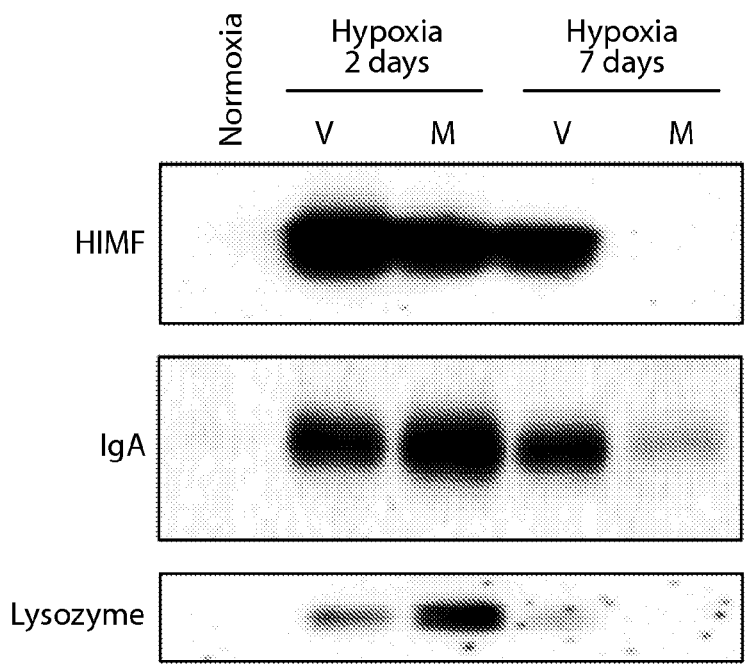
Figure 10A:
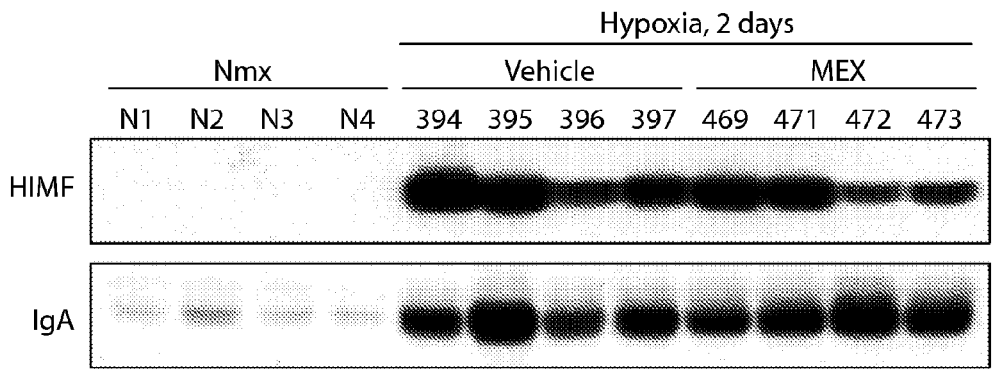
FIG. 10. MSCs-derived exosome suppress hypoxia-induced secretion of HIMF/FIZZ-1/Retnlα in the lung. Mice injected either with 10 μg of MEX (M) or vehicle (V) by tail vein were exposed over indicated time periods to monobaric hypoxia (8.5% $O_2$). 10 μg BAL proteins from each individual mouse were separated on 14% polyacrylamide gel electrophoresis (A, B). Proteins in BAL normalized by quantity from each individual mouse in the same group were pooled and separated on 14% polyacrylamide gel electrophoresis (C). Levels of HIMF, lysozyme, and IgA were evaluated by western blot analysis using specific antibodies.
Figure 10B:
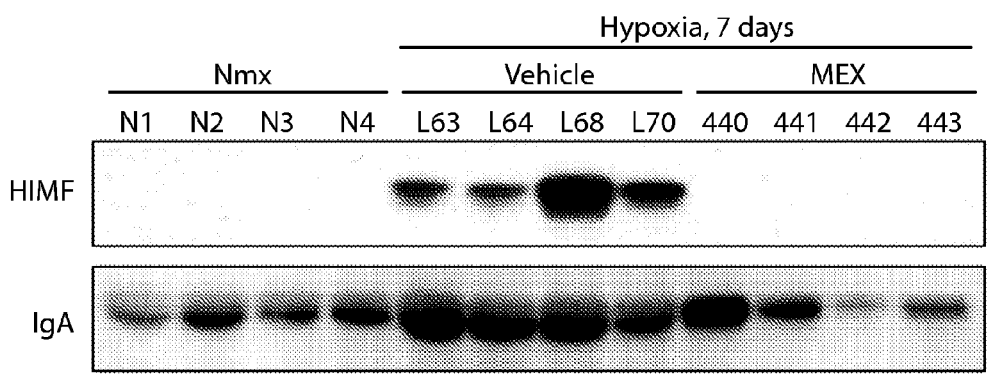
Figure 10C:
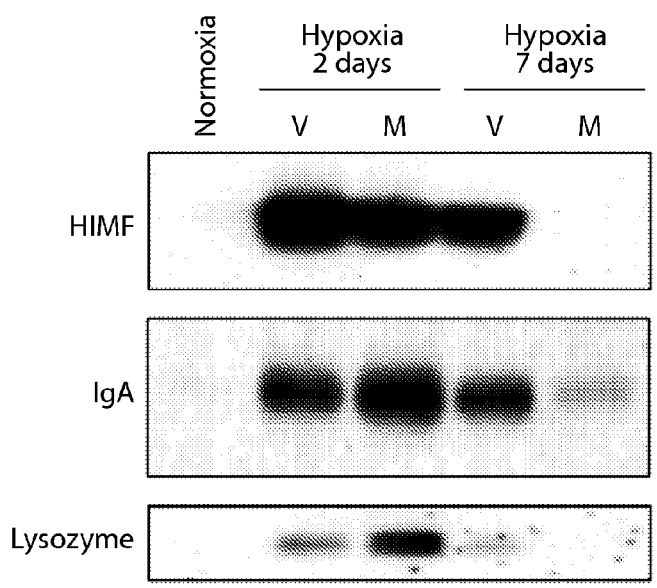
Figure 11A:
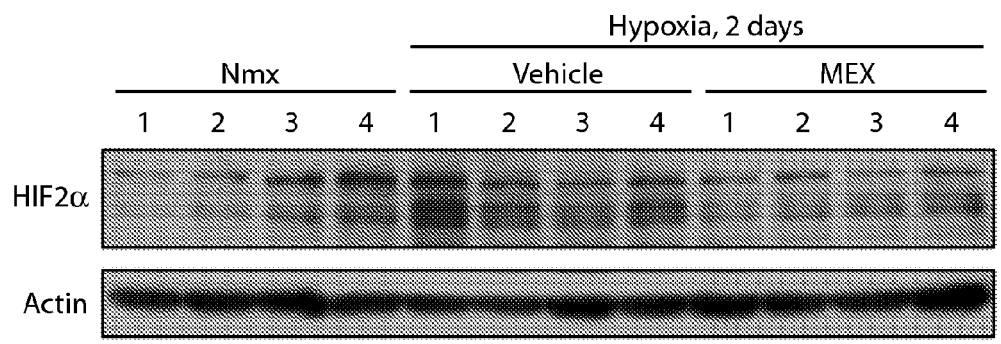
FIG. 11. MSCs-derived exosomes suppress hypoxia-induced upregulation of HIF2α in the lung tissue. Mice injected with either 10 μg MEX or vehicle by tail vein were exposed over indicated time periods to monobaric hypoxia (8.5% $O_2$). Equivalent amount of proteins from individual lung tissue homogenate were separated on denaturing polyacrylamide gel electrophoresis. Levels of HIF2α and actin were detected by western blot analysis using specific antibodies (A, B). Relative intensities for HIF2α/actin were evaluated by densitometric analysis (C). **, p<0.01 vs. normoxia (n=4±SD, One-way ANOVA); ##, p<0.01 vs. vehicle (hypoxia, 2 days) (n=4±SD, One-way ANOVA).
Figure 11B:
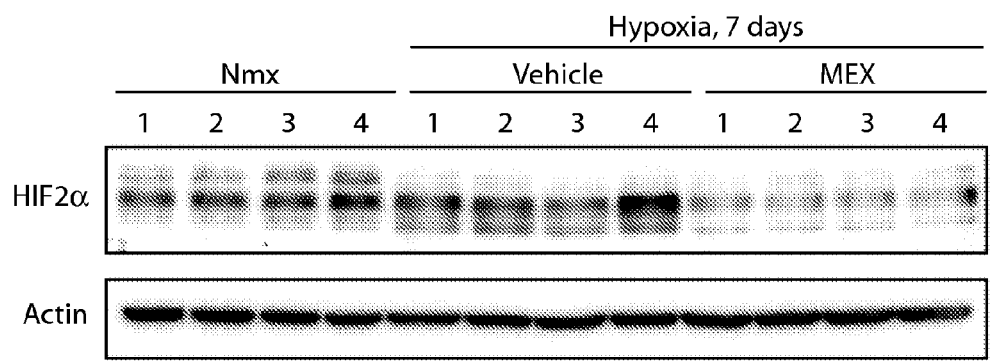
Figure 11C:
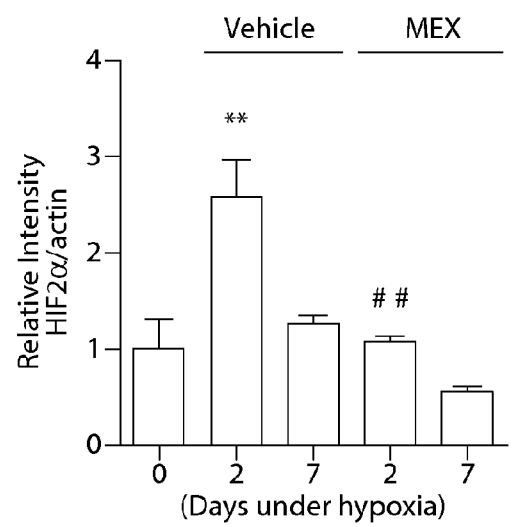
Figure 12A:
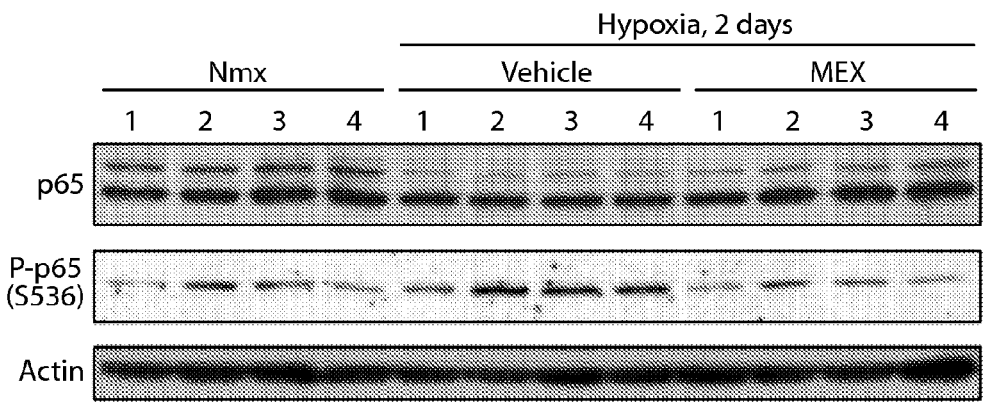
FIG. 12. MSCs-derived exosomes suppress hypoxia-induced activation of NFkB p65 in the lung tissue. Mice injected with either 10 μg MEX or vehicle by tail vein were exposed over indicated time periods to monobaric hypoxia (8.5% $O_2$). Equivalent amount of proteins from individual lung tissue homogenate were separated on denaturing polyacrylamide gel electrophoresis. Levels of p65, phosphorylated-p65 (S536), and actin were detected by western blot analysis using specific antibodies (A, B). Relative intensities for P-p65/actin were evaluated by densitometric analysis (C). *, p<0.05 vs. normoxia (n=4±SD, One-way ANOVA); ##, p<0.01 vs. vehicle (hypoxia, 2 days) (n=4±SD, One-way ANOVA).
Figure 12B:
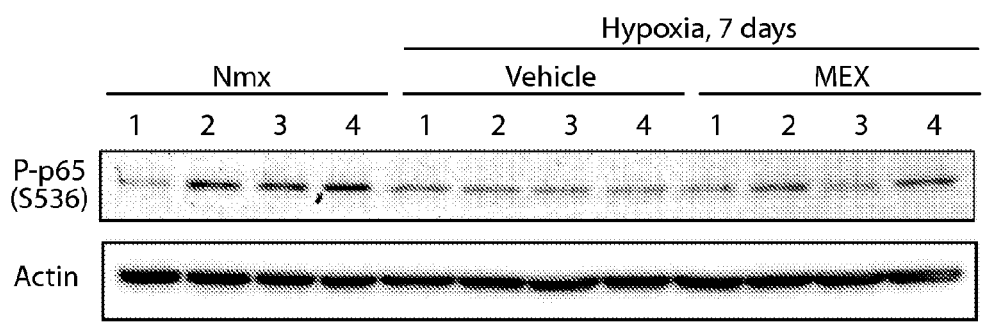
Figure 12C:
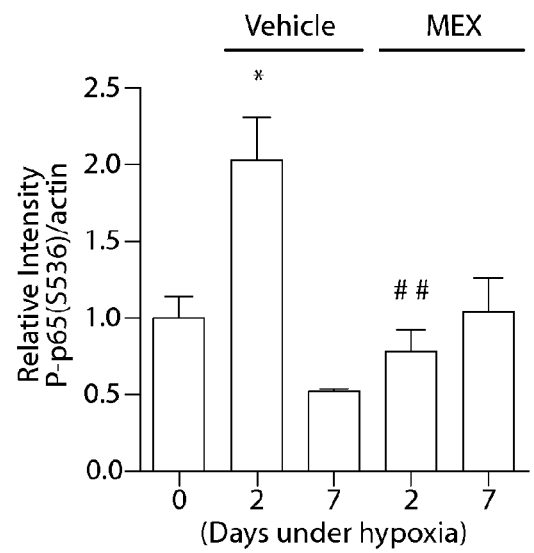
Figure 13A:
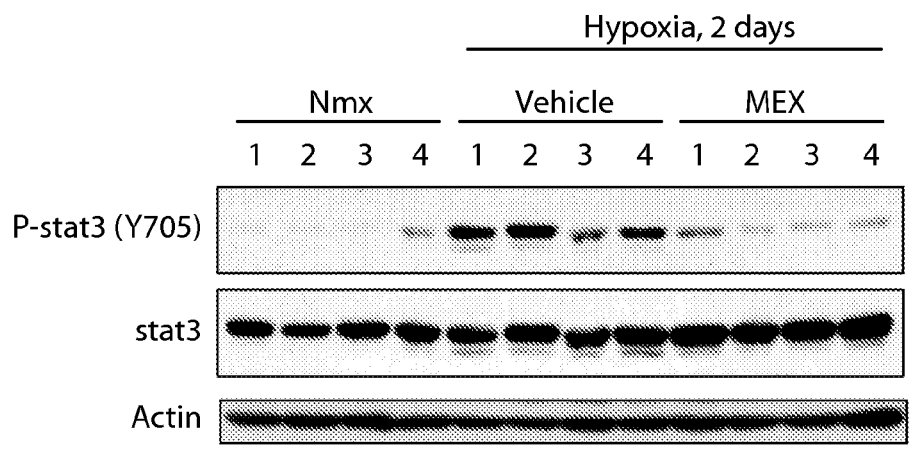
FIG. 13. MSCs-derived exosomes suppress hypoxia-induced activation of STAT3 in the lung tissue. Mice injected with either 10 μg MEX or vehicle by tail vein were exposed to monobaric hypoxia (8.5% $O_2$) for 2 days. Equivalent amount of proteins from individual lung tissue homogenates were separated on denaturing polyacrylamide gel electrophoresis. Levels of STAT3, phosphorylated-STAT3 (Y705) and actin were detected by western blot analysis using specific antibodies (A). Relative intensities for P-STAT3/STAT3 were evaluated by densitometric analysis (B). **, $p<0.01$ vs. normoxia (n=4±SD, One-way ANOVA); ##, $p<0.01$ vs. vehicle (n=4±SD, One-way ANOVA).
Figure 13B:
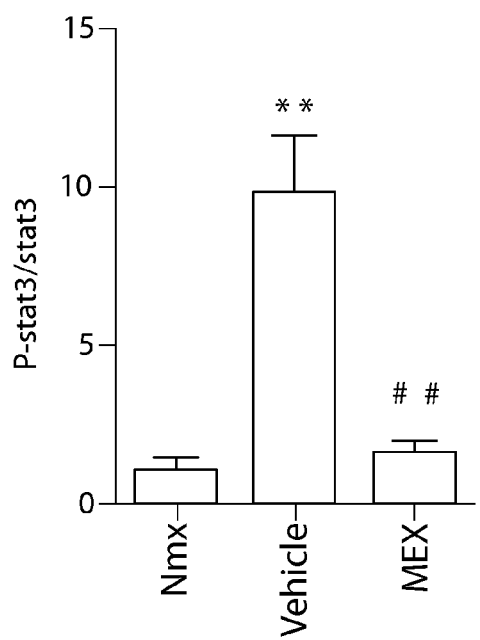
Figure 14A:
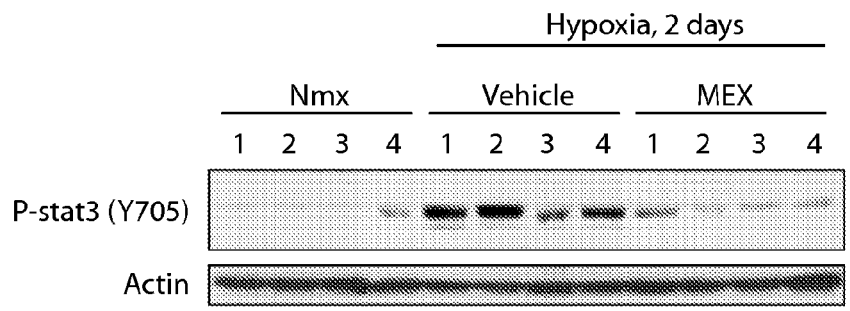
FIG. 14. MSCs-derived exosomes suppress hypoxia-induced activation of STAT3 in the lung tissue. Mice injected with either 10 μg MEX or vehicle by tail vein were exposed over indicated time periods to monobaric hypoxia (8.5% $O_2$). Equivalent amount of proteins from individual lung tissue homogenate were separated on denaturing polyacrylamide gel electrophoresis. Levels of phosphorylated-STAT3 (Y705) and actin were detected by western blot analysis using specific antibodies (A, B). Relative intensities for P-STAT3/actin were evaluated by densitometric analysis (C). ***, $p<0.001$ vs. normoxia or vehicle (hypoxia, 7 days), or MEX (hypoxia, 2 and 7 days) (n=4±SD, One-way ANOVA); ###, $p<0.001$ vs. vehicle (hypoxia, 2 days) (n=4±SD, One-way ANOVA); ns normoxia vs. MEX (hypoxia, 2 days) (n=4±SD, One-way ANOVA).
Figure 14B:
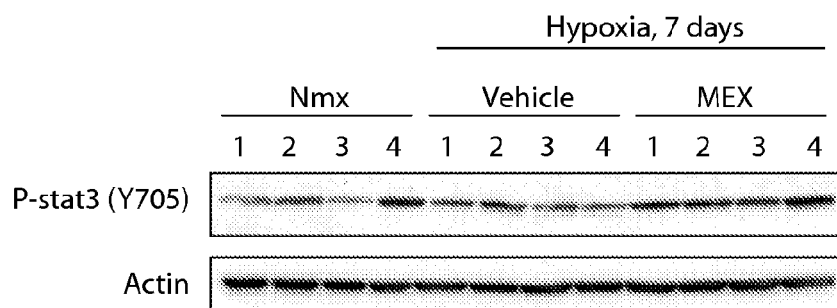
Figure 14C:
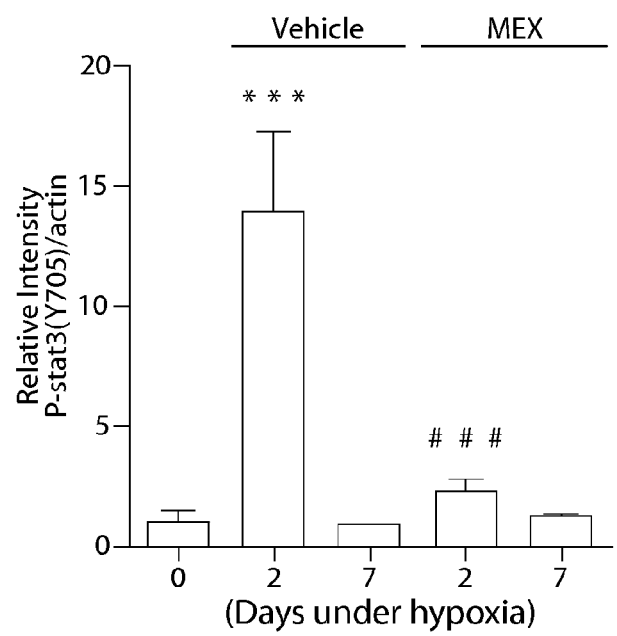
Figure 15A:
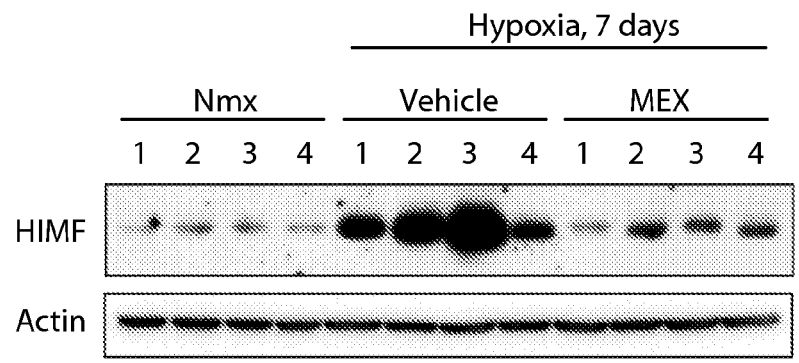
FIG. 15. MSCs-derived exosomes suppress hypoxia-induced HIMF upregulation in the lung tissue. Mice injected with either 10 μg MEX or vehicle by tail vein were exposed to monobaric hypoxia (8.5% $O_2$) for 7 days. Equivalent amount of proteins from individual lung tissue homogenate were separated on denaturing polyacrylamide gel electrophoresis. Levels of HIMF and actin were detected by western blot analysis using specific antibodies (A). Relative intensities for HIMF/actin were evaluated by densitometric analysis (B). **, $p<0.01$ vs. normoxia (n=4±SD, One-way ANOVA); #, $p<0.05$ vs. vehicle (n=4±SD, One-way ANOVA); statistically non-significant between MEX vs. normoxia (n=4±SD, One-way ANOVA).
Figure 15B:
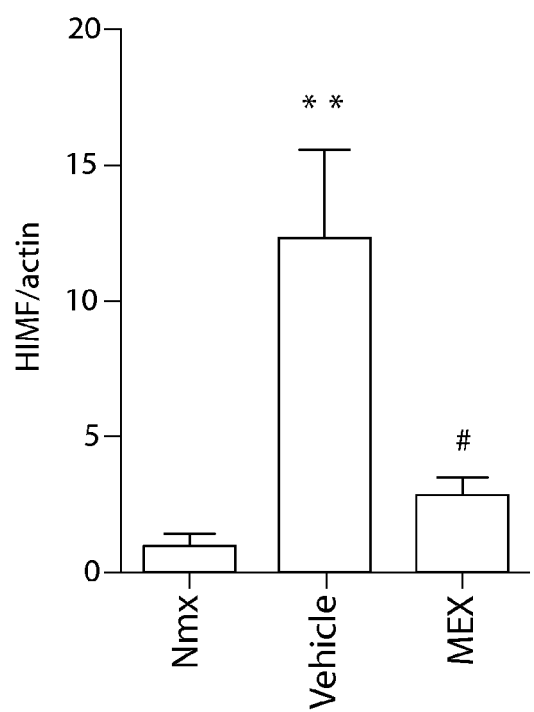
Figure 16A:
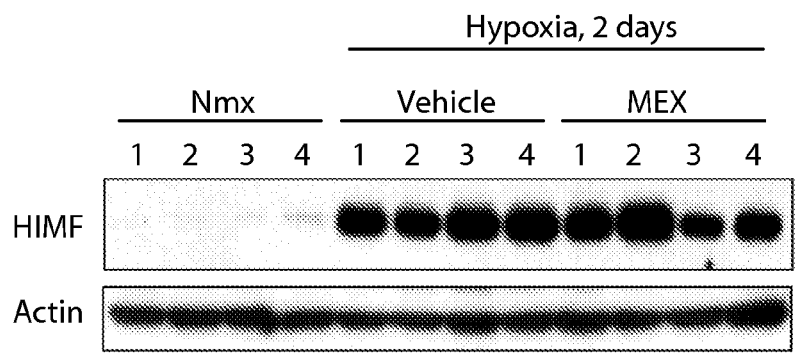
FIG. 16. MSCs-derived exosomes suppress hypoxia-induced HIMF upregulation in the lung tissue. Mice injected with either 10 μg MEX or vehicle by tail vein were exposed over indicated time periods to monobaric hypoxia (8.5% $O_2$). Equivalent amount of proteins from individual lung tissue homogenate were separated on denaturing polyacrylamide gel electrophoresis. Levels of HIMF and actin were detected by western blot analysis using specific antibodies (A, B). Relative intensities for HIMF/actin were evaluated by densitometric analysis (C, D). *, $p<0.001$ vs. normoxia (n=4±SD, One-way ANOVA); , $p<0.01$ vs. normoxia (n=4±SD, One-way ANOVA); #, $p<0.05$ vs. vehicle (n=4±SD, One-way ANOVA).
Figure 16B:
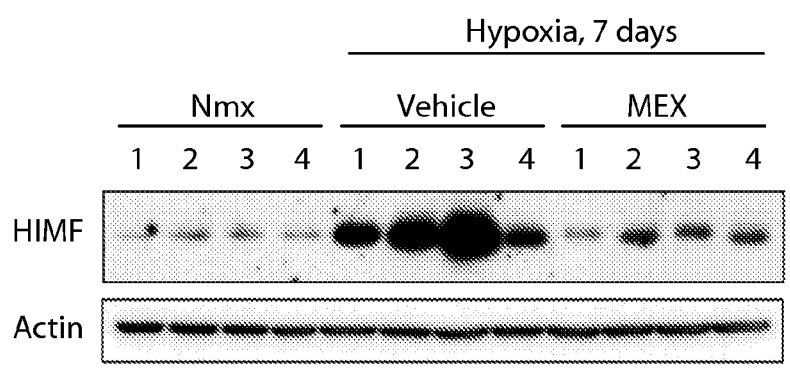
Figure 16C:
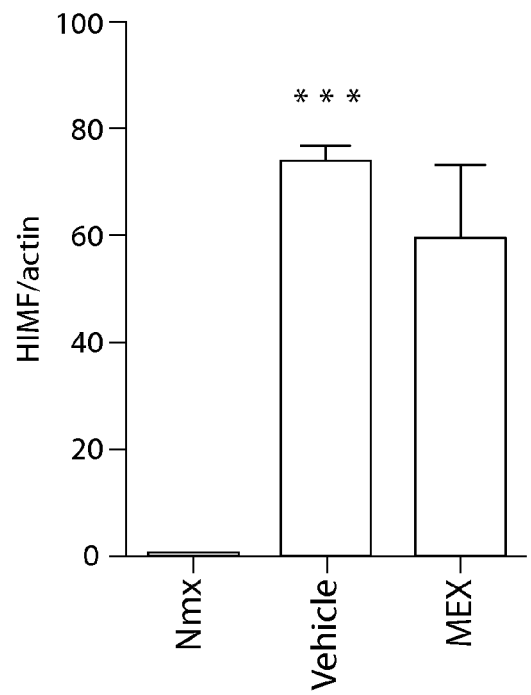
Figure 16D:
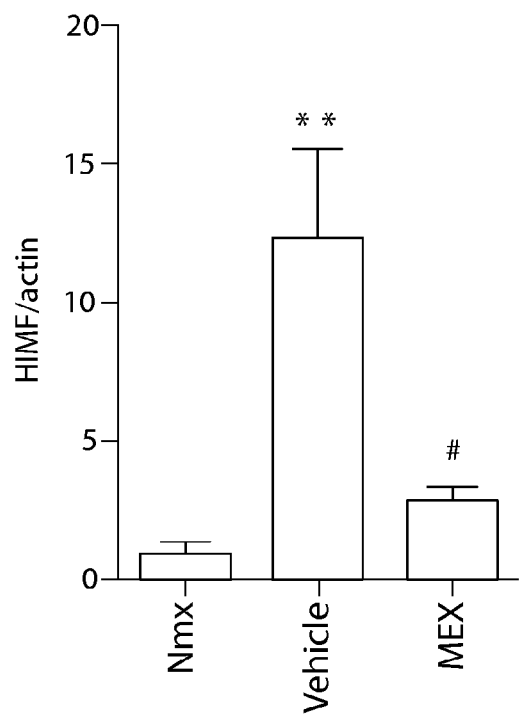
Figure 17A:
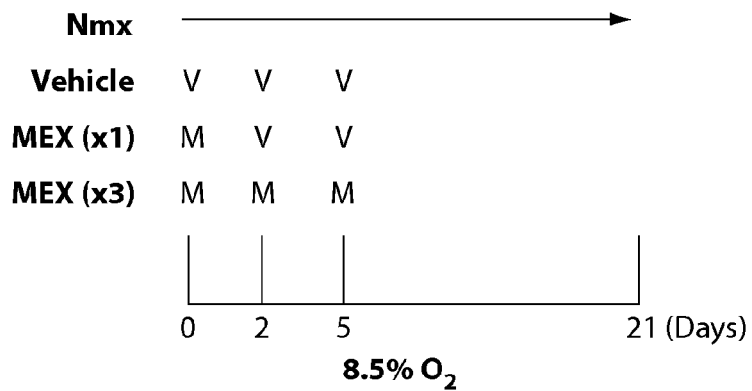
FIG. 17. MSCs-derived exosomes protect chronic hypoxia-induced right heart hypertrophy. Mice injected with either 10 μg MEX (M) or vehicle (V) by tail vein at indicated time periods were exposed to monobaric hypoxia (8.5% $O_2$) for 3 weeks (A). Hearts from individual mouse were processed then ratio of RV/(LV+S) were measured (B). ***, $p<0.001$ vs. normoxia (n=9, One-way ANOVA); ###, $p<0.001$ vs. vehicle (n=11, One-way ANOVA); statistically non-significant between MEX and normoxia (One-way ANOVA).
Figure 17B:
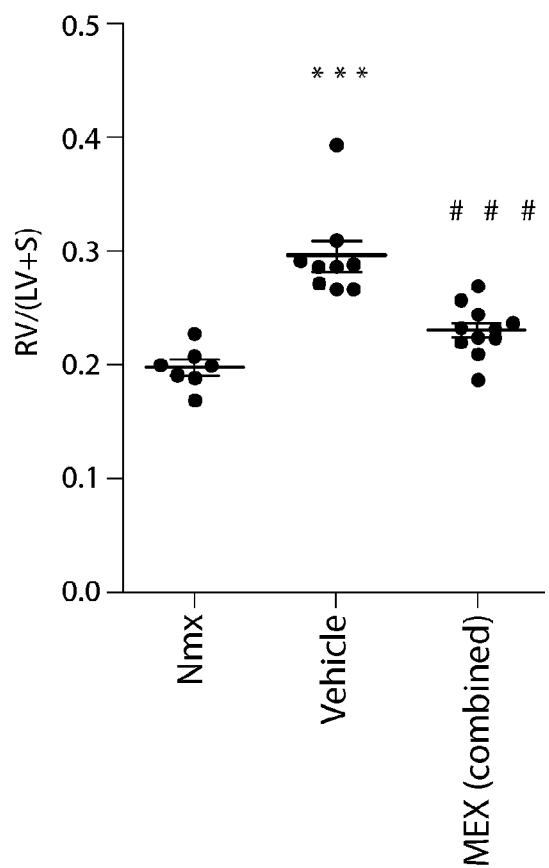
Figure 18:
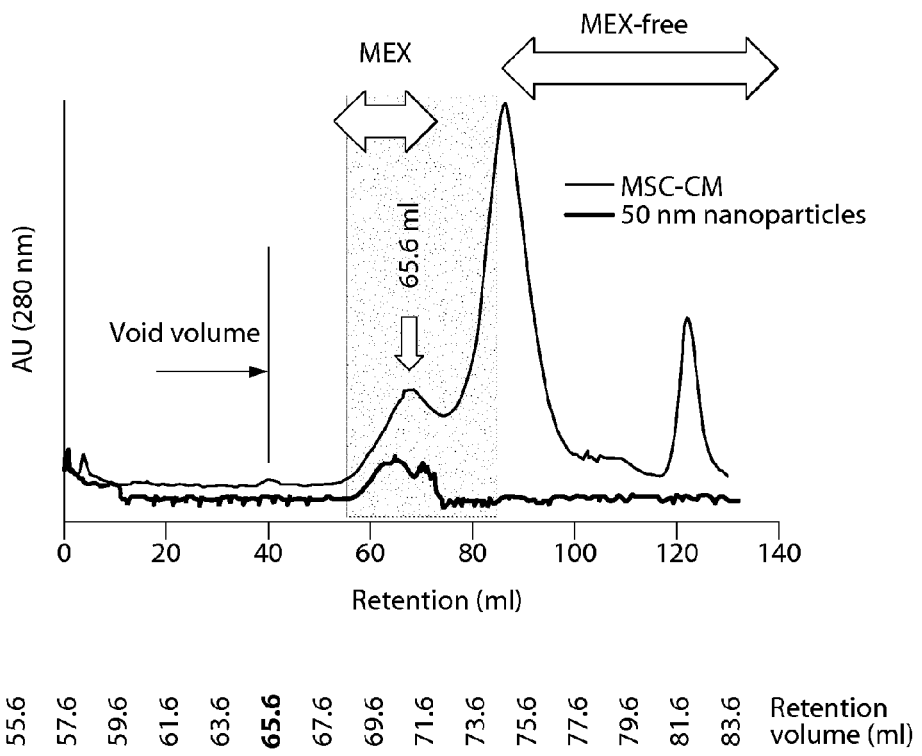
FIG. 18. High resolution profile of MSC exosome purification by FPLC (Fast Protein Liquid Chromatography). Upper panel: Fast Protein Liquid Chromatography of MSC exosome purification. Matrix: HiPrep Sephracyl S-400. Mobile Phase Phosphate Buffered Saline, 300 mM. Flow rate: 0.5 ml/min. Concentrated conditioned media were applied to the column and the eluted protein was monitored by A280. Isolated MSC exosomes (MEX) eluted at 65.5 ml. A molecular size standard of nanoparticles of 50 nm diameter co-eluted with MSC exosomes. Lower panel: Fractions of the eluated were applied to a native polyacrylamide electrophoresis gel and subsequently stained for total protein. The MEX fraction migrated as high MW forms, distinct from bulk protein in the conditioned media.

In this study, we observed that MCP-1 and HIMF were significantly upregulated by hypoxia in the lung and that the hypoxia-induced upregulation was markedly attenuated by treatment of MEX. Therefore, we hypothesized that MEX might prevent hypoxia-induced PAH by blocking both important mediators of PAH. To test the hypothesis, mice were exposed to hypoxia for 3 weeks after receiving either MEX or FEX or PBS as control. At the end of experimental period, RVSP was measured and heart tissue was processed for RV hypertrophy. FIGS. 5B and 5C showed that all the hypoxic mice exhibited elevated RVSP and Fulton's Index compared with age-matched normoxic mice. In contrast, significant improvement was observed for the mice that received MEX as compared to the mice that received either PBS or FEX. Moreover, compared with mice that received a single injection of MEX, mice that received additional injections of MEX at day 4 showed significantly reduced RVSP and RV hypertrophy under chronic hypoxia, indicating repeated administration of MEX ameliorates pulmonary artery pressure and ventricular wall thickness in response to chronic hypoxia. To investigate whether multiple treatments of MEX could attenuate hypoxia-induced pulmonary vascular remodeling, histological sections of the hypoxic lungs were morphometrically analyzed by staining pulmonary vessels with alpha-SMA antibody (FIG. 5D). The percentage of medial vessel wall thickness of small pulmonary arterioles within a range of 20~30 μm in diameter was determined. In comparison with age-matched normoxic control mice, markedly increased thickness of small pulmonary arterioles by chronic hypoxia was observed in either PBS or FEX treated mice while no significant difference was observed for the vessel wall thickness between the control and MEX treated mice, indicating that MEX are able to prevent the process of hypoxia-induced pulmonary vascular remodeling (FIG. 5E).

MEX Comprise a Variety of Immunomodulatory Factors.

We have observed dramatic effects of MEX on both hypoxia-induced acute pulmonary inflammation and pulmonary artery hypertension by chronic hypoxia. To investigate their molecular mechanism, we performed global proteomic profiling of both MEX and FEX by high performance liquid chromatography mass spectrometry (HPLC-MS/MS). A total of 273 proteins were identified with high confidence in MEX and 35% of proteins were also detected in FEX. To achieve high confidence for profiling considerable proteins associated with MEX, we identified proteins with high (>25) number of MS/MS spectra and high (>3) ratio of MEX/FEX in sequence coverage. 8 proteins fit this criterion and these are listed in Table 1. Among these proteins, 3 were unique and 5 were highly enriched in MEX. Galectin-3-binding protein (LGALS3BP/MAC2BP), which is one of the unique proteins in MEX, is a secretory protein that has been shown to possess immunomodulatory activities by inhibiting transcription of TH2 cytokine which is hallmark of athma[34]. It is able to interact with a variety of proteins on the cellular surface and matrix including the lectin family, integrins, laminins, and fibronectin. As the interactions have been implicated in modulating tumor cell adhesion to extracellular proteins[35], GAL3BP on the surface of MEX might play an important role to target the infused MEX to the surface of recipient cells in a ligand specific manner. Another unique protein in MEX, thrombospondin-2, is known to act as a potent endogenous inhibitor of tumor growth and angiogenesis[36] and to suppress the production of pro-inflammatory cytokines IFN-γ and TNF-α[37]. Lactadherin (MFGE8), a major component of dendritic cell-derived exosomes[38], has been reported to play a role in cell death and apoptosis where it recognizes specifically phosphatidylserine exposed on apoptotic cells and promotes phagocytic clearance of apoptotic cells by binding to cells expressing integrin$_{\alpha V}$ and integrinp$_{63}$[39,40]. On the surface of MEX, lactadherin may be involved in targeting MEX to their recipient cell types. Moreover, it has been reported that lactadherin is also involved in phagocytic clearance of amyloid beta-peptide (Abeta), which is a major component in accumulated senile plaques in Alzheimer's disease, by direct protein-protein interaction. The abundance of Abeta in exosomal fraction is possibly due to direct interaction between lactadherin and Abeta. Adipocyte-enhancer-binding protein 1(AEBP1), also called aortic carboxypeptidase-like protein (ACLP), plays important physiological roles in wound healing and energy homeostasis. Mice lacking exons 7-16 exhibit deficient wound healing and AEBP1-null mice are resistant to diet-induced obesity[41]. Table 1 and FIG. 22 describe the various mediators identified in mouse and human MEX.

MEX of Either Mouse or Human Origin Mediate the Suppression of STAT3 Activation by Hypoxia.

Figure 19A:
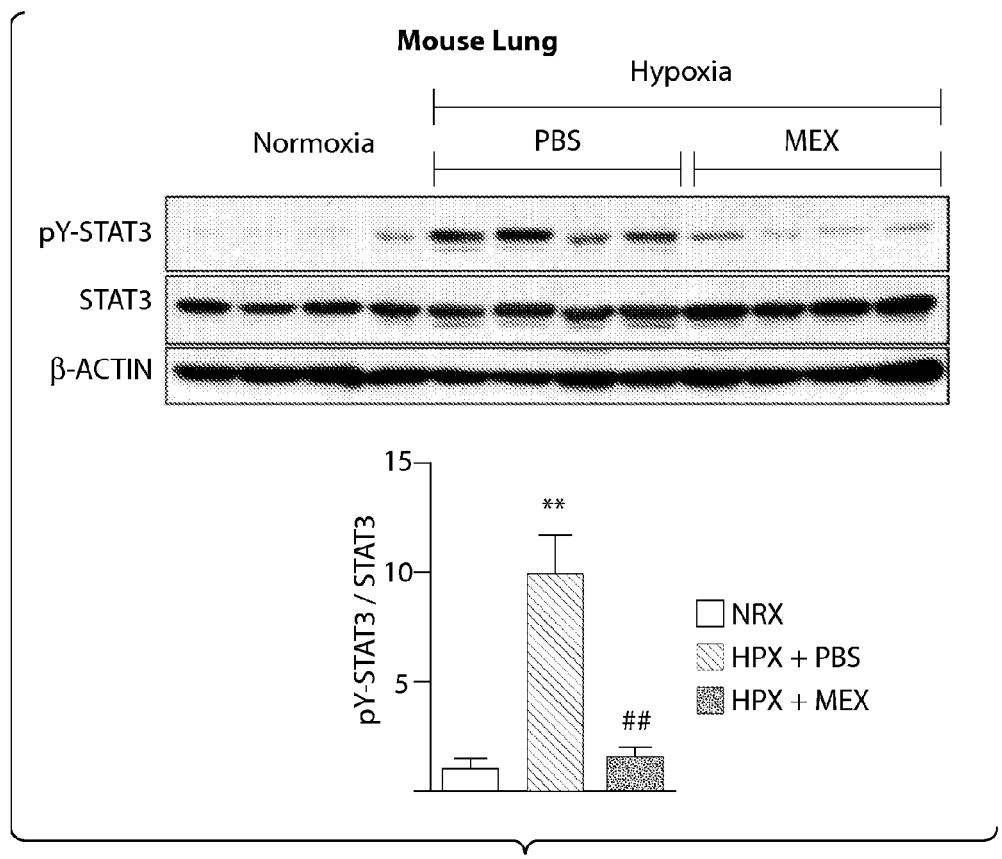
FIG. 19. MEX of either mouse or human origin suppress the hypoxic activation of STAT3. (A) Total protein extracts from lungs of individual animals treated with 10 μg MEX preparations. Right Panel: Hypoxia exposure for 2 days resulted in activation of STAT3 through phosphorylation at Tyr-705 (pY-STAT3) in mouse lung, and this was prevented by treatment with MEX of mouse origin. Right panel: Quantitation of STAT3 activation. For all groups, n=4, One-way ANOVA: , $p<0.01$ vs. Normoxia. , $p<0.01$ vs. PBS. (B) Primary cultures of human Pulmonary Artery Endothelial Cells (hPAECs) exposed to hypoxia (1% $O_2$, 5 hrs) exhibit robust activation of STAT3 that is efficiently suppressed in the presence of MEX secreted by MSCs from human umbilical cord stroma (hUC-MEX). The microvesicle-depleted fraction of media conditioned by hUC-MSCs (hUC-ExD-CM) has no effect on STAT3 activation.

Early hypoxia resulted in activation of STAT3 in the mouse lung, through phosphorylation at Tyr-705, and without any effect on the total levels of STAT3 protein. This activation was efficiently suppressed by MEX treatment (FIG. 19A). STAT3 is a transcription factor integral to signaling pathways of many cytokines and growth factors and STAT3 activation plays a critical role in respiratory epithelial inflammatory responses. Importantly, persistent ex vivo STAT3 activation, has been linked to the hyperproliferative and apoptosis-resistant phenotype observed in PAECs (Masri, F. A. et al., 2007, *Am J Physiol Lung Cell Mol Physiol* 293:L548-554) and pulmonary artery smooth muscle cells (PASMCs) (Paulin, R. et al., 2011, *Circulation* 123:1205-1215) from patients with idiopathic pulmonary arterial hypertension (IPAH). Therefore, suppression of hypoxic STAT3 activation could account for the pleiotropic protective effects of MEX treatment.

Figure 19B:
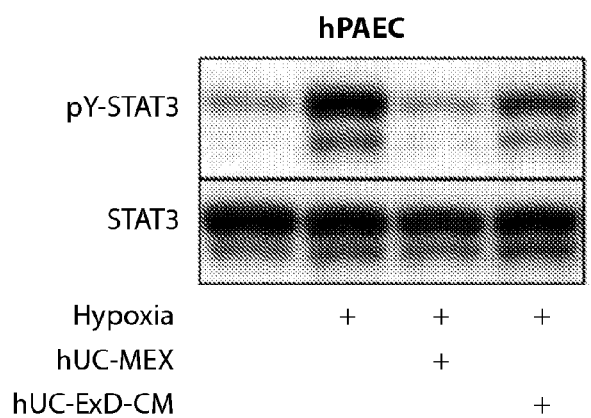

To verify that the suppression of this hypoxic signaling is not a property specific to MEX of mouse origin, MSCs from human umbilical cord stroma (hUC-MSC) (Mitchell, K. E. et al. and Penolazzi, L. et al.) were isolated and exosome-enriched (hUC-MEX) and exosome-depleted (hUC-ExD-CM) fractions were prepared from hUC-MSC conditioned media through size exclusion chromatography, as described herein. As depicted in FIG. 19B, exposure of hPAECs to hypoxia results in robust activation of STAT3 by Tyr-705 phosphorylation. Treatment with hUC-MEX completely abrogated this response, whereas the fraction depleted of microvesicles had no effect. In addition to demonstrating that suppression of STAT3 activation is a property shared by MEX of both human and mouse origin, these results strongly suggest that direct suppression of hypoxic signaling in pulmonary vascular cells is a primary function underlying the protection conferred by MEX treatment.

MEX Treatment Suppresses the Hypoxic Induction of the miR-17 microRNA Superfamily and Increases Levels of Anti-Proliferative miR-204 in the Lung.

Figure 20A:
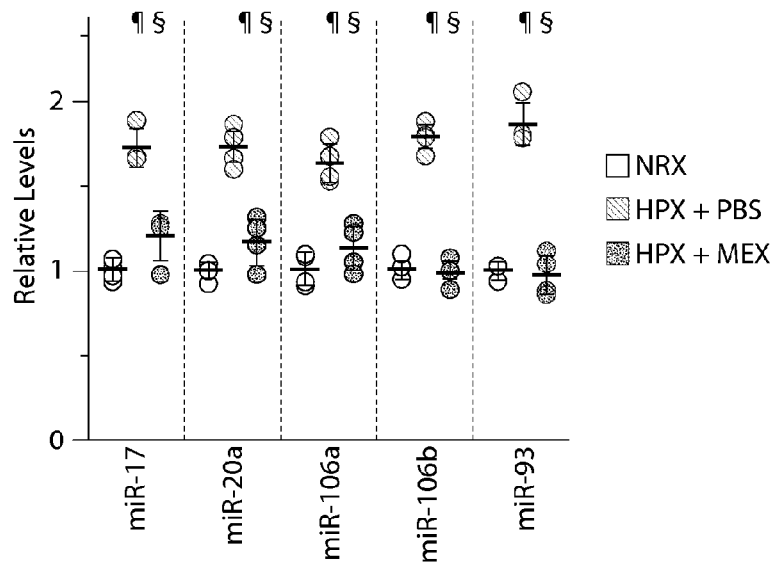
FIG. 20. MEX treatment suppresses the hypoxic induction of the miR-17 microRNA superfamily and increases levels of anti-proliferative miR-204 in the lung. MicroRNA levels in total mouse lung from animals treated with 10 μg MEX preparations. miR levels were assessed by qPCR at 7 days of hypoxic exposure and are presented relative to the mean of the normoxic group. (A) Select miRs representing the miR-17~92, miR-106b~25 and miR-106a~363 clusters. (B) Select miRs reported to be involved in hypoxic signaling. (C) Upregulation of basal levels of the pulmonary arteriole-specific miR-204 upon MEX treatment. Dots represent expression levels in individual animals. NRX: Normoxia; HPX: Hypoxia. For all groups, n=4, One-way ANOVA: **, $p<0.01$; ¶, $p<0.001$ vs. Normoxia. §, $p<0.001$ vs. PBS.
Figure 20B:
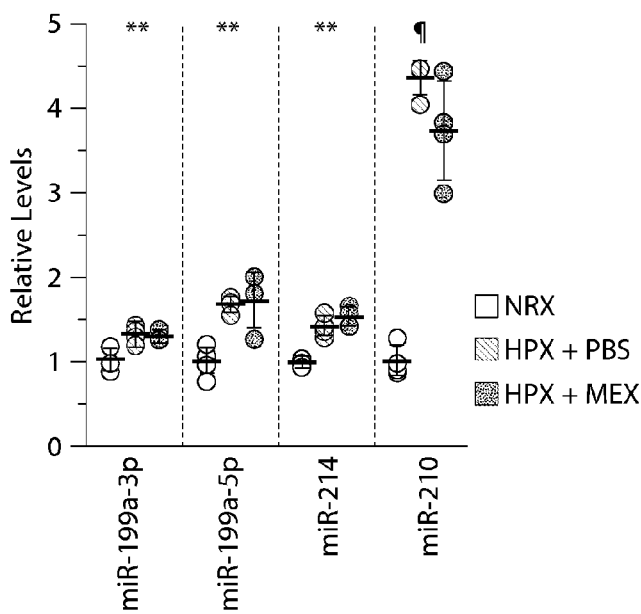

STAT3 (activated by either VEGF or IL-6) has been reported to directly regulate the transcription of the miR-17~92 cluster of microRNAs in PAECs, resulting in decreased levels of bone morphogenetic protein receptor-2 (BMPR2), a target of miR-17 (Brock, M. et al., 2009, *Circ Res* 104:1184-1191). Therefore, we assessed the effect of hypoxia and MEX treatment on the miR-17~92 cluster of microRNAs and its conserved paralog clusters, miR-106b~25 and miR-106a~363. These microRNA clusters have been postulated to be pro-proliferative, targeting an array of genes involved in the G1/S phase transition (Cloonan, N. et al., 2008, *Genome Biol* 9:R127) and have been reported to play a central role in embryonic lung morphogenesis (Carraro, G., 2009, *Dev Biol* 333:238-250). We found that select microRNAs representing all three clusters of the miR-17 superfamily were upregulated by hypoxia in the lung, and this transcriptional activation was efficiently suppressed by MEX treatment (FIG. 20A). Interestingly, levels of microRNAs involved in hypoxic signaling networks, such as miR-199a-5p, a microRNA reported to stabilize HIF1α in cardiac myocytes (Rane, S. et al., 2009, *Circ Res* 104:879-886), miR-214, which shares the same host gene with miR-199 (Watanabe, T. et al., 2008, *Dev Dyn* 237:3738-3748), or miR-210, a hypoxamir under direct HIF1α regulation (Chan, S. Y. et al., 2010, *Cell Cycle* 9:1072-1083), were not affected by MEX treatment (FIG. 20B), pointing to targeted effects of MEX on specific hypoxia-regulated signaling pathways.

Figure 20C:
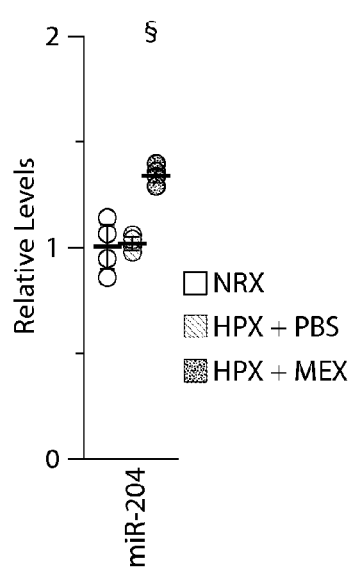
Figure 21:
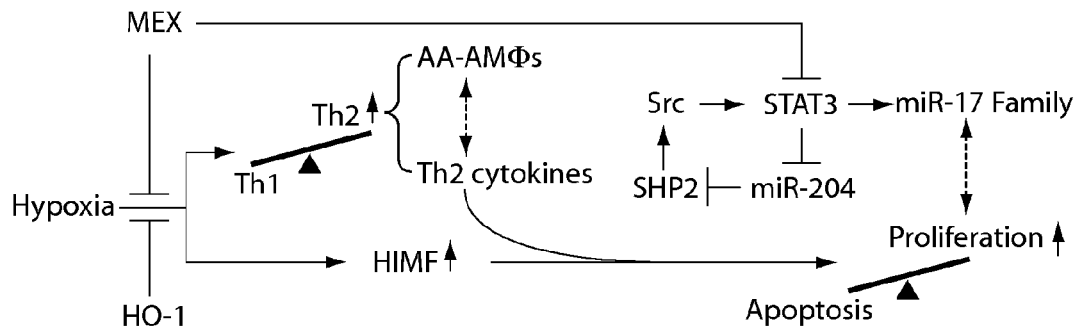
FIG. 21. Schema of one non-limiting hypothesis synthesizing the results of this study. Hypoxia shifts the Th1/Th2 balance of immunomodulators in the lung, resulting in alternative activated alveolar macrophages (AA-AMφ) and, in the early phase, induces the expression of HIMF in the lung epithelium. HIMF mitogenic action on the vasculature requires Th2 cytokines, such as IL-4. Consequences of the shift towards proliferation include the hypoxic activation of STAT3 signaling and the upregulation of the miR-17 family of microRNAs. Treatment with MEX interferes with an early hypoxic signal in the lung, suppressing both inflammation and HIMF transcriptional upregulation. It addition, MEX treatment may directly upregulate miR-204 levels, thus breaking the STAT3-miR-204-STAT3 feed-forward loop, and shifting the balance to an anti-proliferative state.

Importantly, we observed that MEX treatment resulted in the increase of lung levels of miR-204, (FIG. 20C) a microRNA enriched in distal pulmonary arteries that is transcriptionally suppressed by STAT3 but also inhibits the activation of STAT3 in a feed-forward regulatory loop (Courboulin, A. et al., 2011, *J Exp Med* 208:535-548). The proliferative and anti-apoptotic phenotype of PASMCs isolated from patients with IPAH is inversely related to the level of miR-204 and delivery of exogenous miR-204 to the lungs of animals with PH ameliorated established disease. Therefore, we interpret these results as an indication that MEX treatment, by suppressing STAT3 activation at the early stages of hypoxic exposure, prevents the hypoxic induction of the pro-proliferative miR-17 superfamily in the lung vasculature and blocks the STAT3-miR-204-STAT3 feed-forward loop in distal pulmonary vessels. This shifts the balance towards an anti-proliferative state in the lung vasculature and prevents vascular remodeling under chronic hypoxia. FIG. 21 is a schematic representation of the hypoxic signaling pathways proposed to be operative in the development of PH that are modulated by MEX.

In summary, MSC-conditioned media was fractionated through size-exclusion chromatography to identify the biologically-active component protecting against hypoxia-induced lung inflammation and HPH. It was found that MEX are the critical vectors of MSC action: MEX efficiently suppressed the hypoxic pulmonary influx of macrophages and blocked the upregulation of the pro-inflammatory and mitogenic mediators such as MCP-1, IL-6, and hypoxia-induced mitogenic factor (HIMF; FIZZ1/RELM-α/RETNLA) in the hypoxic lung. Pro-proliferative pathways activated in the hypoxic lung were also blocked by MEX treatment, as evidenced by the suppression of signal transducers and activators of transcription (STAT3). This resulted in increased lung levels of miR-204, a microRNA enriched in distal pulmonary arterioles that is down-regulated in both human PH and in experimental models of disease (Courboulin, A. et al.). It was also found that hypoxia upregulates members of the miR-17 family of microRNA clusters in lung tissue, microRNAs shown to be under the regulatory control of STAT3, and that MEX treatment efficiently suppresses this pro-proliferative signal. MEX isolated from the culture media of human umbilical cord-derived MSCs had similar inhibitory effect on hypoxic proliferative signaling pathways as the mouse MEX. Human MEX significantly inhibited the hypoxic activation of STAT3 in cultured hPAECs. In contrast, exosome-depleted MSC-culture media had no physiologic effect in vivo nor on cultured cells in vitro, pointing to MEX as the key effectors of MSC paracrine function.

TABLE 2

Purification of MSCs-derived exosomes

| Step | Volume | Concentration | Total protein (mg) | Yield (%) |
|---|---|---|---|---|
| Serum-free MSCs-conditioned | 25 | 28.91 | 7,228 | 100 |
| Ultrafiltration (100 kDa MWCO) | 1 | 7,184.70 | 7,185 | 99.4 |
| S-400 column chromatography | 4.5 | 166 | 747 | 10.4 |

REFERENCES

1. Dominici, M., et al., *Cytotherapy* 8, 315-317 (2006).
2. Minamino, T., et al., *Proc Natl Acad Sci USA* 98, 8798-8803 (2001).
3. Steiner, M. K., et al. *Circ Res* 104, 236-244, 228p following 244 (2009).
4. Egashira, K., et al., *FASEB J* 14, 1974-1978 (2000).
5. Ikeda, Y., et al., *Am J Physiol Heart Circ Physiol* 283, H2021-2028 (2002).
6. Teng, X., et al., *Circ Res* 92, 1065-1067 (2003).
7. Angelini, D. J., et al., *Am J Physiol Lung Cell Mol Physiol* 296, L582-593 (2009).
8. Yamaji-Kegan, K., et al., *Am J Physiol Lung Cell Mol Physiol* 291, L1159-1168 (2006).
9. Daley, E., et al., *J Exp Med* 205, 361-372 (2008).

10. Angelini, D. J., et al., *Am J Respir Cell Mol Biol* 41, 553-561 (2009).
11. Rojas, M., et al., *Am J Respir Cell Mol Biol* 33, 145-152 (2005).
12. Ortiz, L. A., et al., *Proc Natl Acad Sci USA* 100, 8407-8411 (2003).
13. Xu, J., et al., *Am J Physiol Lung Cell Mol Physiol* 293, L131-141 (2007).
14. Baber, S. R., et al., *Am J Physiol Heart Circ Physiol* 292, H1120-1128 (2007).
15. Aslam, M., et al., *Am J Respir Crit Care Med* 180, 1122-1130 (2009).
16. van Haaften, T., et al., *Am J Respir Crit Care Med* 180, 1131-1142 (2009).
17. Lee, R. H., et al., *Cell Stem Cell* 5, 54-63 (2009).
18. Lee, J. W., et al., *Proc Natl Acad Sci USA* 106, 16357-16362 (2009).
19. Valadi, H., et al., *Nat Cell Biol* 9, 654-659 (2007).
20. Aoki, N., et al., *Endocrinology* 148, 3850-3862 (2007).
21. Segura, E., et al., *J Immunol* 179, 1489-1496 (2007).
22. Viaud, S., et al., *PLoS One* 4, e4942 (2009).
23. Kovar, M., et al., *Proc Natl Acad Sci USA* 103, 11671-11676 (2006).
24. O'Neill, H. C. & Quah, B. J., *Sci Signal* 1, pe8 (2008).
25. Girl, P. K. & Schorey, J. S., *PLoS One* 3, e2461 (2008).
26. Yu, S., et al., *J Immunol* 178, 6867-6875 (2007).
27. Chalmin, F., et al., *J Clin Invest* 120, 457-471 (2010).
28. Al-Nedawi, et al., *Proc Natl Acad Sci USA* 106, 3794-3799 (2009).
29. Ratajczak, J., et al., *Leukemia* 20, 847-856 (2006).
30. Yuan, A., et al., *PLoS One* 4, e4722 (2009).
31. Zitvogel, L., et al., *Nat Med* 4, 594-600 (1998).
32. Wieckowski, E. U., et al., *J Immunol* 183, 3720-3730 (2009).
33. Bruno, S., et al., *J Am Soc Nephrol* 20, 1053-1067 (2009).
34. Kalayci, O., et al., *Ann Allergy Asthma Immunol* 93, 485-492 (2004).
35. Ulmer, T. A., et al., *J Cell Biochem* 98, 1351-1366 (2006).
36. Streit, M., et al., *Proc Natl Acad Sci USA* 96, 14888-14893 (1999).
37. Park, Y. W., et al., *Am J Pathol* 165, 2087-2098 (2004).
38. Thery, C., et al., *J Cell Biol* 147, 599-610 (1999).
39. Hanayama, R., et al., *Science* 304, 1147-1150 (2004).
40. Borisenko, G. G., et al., *Cell Death Differ* 11, 943-945 (2004).
41. Ro, H. S., et al., *Obesity (Silver Spring)* 15, 288-302 (2007).
42. Liu, T., et al., *J Immunol* 173, 3425-3431 (2004).
43. Stutz, A. M., et al., *J Immunol* 170, 1789-1796 (2003).
44. Nair, M. G., et al., *J Exp Med* 206, 937-952 (2009).
45. Pesce, J. T., et al., *PLoS Pathog* 5 e1000393 (2009)

EQUIVALENTS

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating a subject having or at increased risk of developing a lung disease, the method comprising administering effective amounts of isolated mesenchymal stem cell (MSC) exosomes and a pulmonary surfactant to said subject, wherein the lung disease is pulmonary hypertension, bronchopulmonary dysplasia (BPD), or idiopathic pulmonary fibrosis.

2. The method of claim 1, wherein the subject has or is at an increased risk of developing schistosomiasis.

3. The method of claim 1, wherein the method further comprises administering to the subject an effective amount of a steroid, an antioxidant, or inhaled nitric oxide.

4. The method of claim 1, wherein the isolated MSC exosomes and the pulmonary surfactant are administered repeatedly to the subject.

5. The method of claim 1, wherein the isolated MSC exosomes are derived from cord blood MSC.

6. The method of claim 1, wherein the isolated MSC exosomes are derived from bone marrow MSC.

7. The method of claim 1, wherein the subject is less than 4 weeks of age.

8. The method of claim 1, wherein the lung disease is pulmonary hypertension.

9. The method of claim 1, wherein the lung disease is idiopathic pulmonary fibrosis.

10. The method of claim 1, wherein the subject is born prematurely.

11. The method of claim 10, wherein the subject is born at less than 35 weeks of gestation.

12. The method of claim 11, wherein the subject is born at less than 26 weeks of gestation.

13. The method of claim 1, wherein the lung disease is BPD.

14. The method of claim 13, wherein the BPD is inflammatory.

15. The method of claim 13, wherein the BPD is non-inflammatory.

* * * * *

UNITED STATES PATENT AND TRADEMARK OFFICE
CERTIFICATE OF CORRECTION

PATENT NO. : 9,901,600 B2
APPLICATION NO. : 14/004237
DATED : February 27, 2018
INVENTOR(S) : S. Alexander Mitsialis et al.

It is certified that error appears in the above-identified patent and that said Letters Patent is hereby corrected as shown below:

In the Specification

At Column 1, Line 20, please replace the paragraph titled FEDERALLY SPONSORED RESEARCH with the following paragraph:

FEDERALLY SPONSORED RESEARCH
This invention was made with government support under grant number HL085446 awarded by the National Institutes of Health. The government has certain rights in the invention.

Signed and Sealed this
Twenty-sixth Day of June, 2018

Andrei Iancu
*Director of the United States Patent and Trademark Office*

UNITED STATES PATENT AND TRADEMARK OFFICE
CERTIFICATE OF CORRECTION

PATENT NO.       : 9,901,600 B2
APPLICATION NO.  : 14/004237
DATED            : February 27, 2018
INVENTOR(S)      : S. Alexander Mitsialis et al.

It is certified that error appears in the above-identified patent and that said Letters Patent is hereby corrected as shown below:

In the Specification

At Column 1, Line 20, please replace the paragraph titled FEDERALLY SPONSORED RESEARCH with the following paragraph:
FEDERALLY SPONSORED RESEARCH
This invention was made with government support under Grant Numbers HL055454 and HL085446, awarded by the National Institutes of Health. The Government has certain rights in the invention.

This certificate supersedes the Certificate of Correction issued June 26, 2018.

Signed and Sealed this
Twentieth Day of August, 2024

Katherine Kelly Vidal
*Director of the United States Patent and Trademark Office*